(12) United States Patent
Abolfathi et al.

(10) Patent No.: US 10,332,164 B2
(45) Date of Patent: Jun. 25, 2019

(54) HEALTH-CARE E-COMMERCE SYSTEMS AND METHODS

(75) Inventors: Amir Abolfathi, Menlo Park, CA (US); Ikechukwu Chibuzo Udechuku, San Francisco, CA (US); Phillips Alexander Benton, Mountain View, CA (US); Beth Ann Cooney, Sunnyvale, CA (US); Keith Wolf, San Francisco, CA (US)

(73) Assignee: Align Technology, Inc., San Jose, CA (US)

(*) Notice: Subject to any disclaimer, the term of this patent is extended or adjusted under 35 U.S.C. 154(b) by 0 days.

(21) Appl. No.: 12/964,565

(22) Filed: Dec. 9, 2010

(65) Prior Publication Data

US 2011/0145015 A1  Jun. 16, 2011

Related U.S. Application Data

(63) Continuation of application No. 11/271,360, filed on Nov. 10, 2005, now Pat. No. 7,904,307, which is a
(Continued)

(51) Int. Cl.
*G06Q 50/00* (2012.01)
*G06Q 30/06* (2012.01)
(Continued)

(52) U.S. Cl.
CPC ............. *G06Q 30/06* (2013.01); *B33Y 50/00* (2014.12); *B33Y 80/00* (2014.12); *G06F 19/00* (2013.01); *G06Q 50/22* (2013.01); *G06Q 50/24* (2013.01)

(58) Field of Classification Search
CPC ........ G05Q 10/00; G06Q 50/00; G06Q 10/00; G16H 10/00; G16H 15/00; G16H 20/00;
(Continued)

(56) References Cited

U.S. PATENT DOCUMENTS 2,467,432 A  4/1949  Kesling
3,407,500 A  10/1968  Kesling
(Continued)

FOREIGN PATENT DOCUMENTS

AU  3031677  5/1979
AU  517102  7/1981
(Continued)

OTHER PUBLICATIONS

Alcaniz, et al., "An Advanced System for the Simulation and Planning of Orthodontic Treatments," Karl Heinz Hohne and Ron Kikinis (eds.), *Visualization in Biomedical Computing*, 4th Int'l. Conf., VBC '96, Hamburg, Germany, Sep. 22-25, 1996, Springer-Verlag, pp. 511-520.
(Continued)

*Primary Examiner* — Robert W Morgan
*Assistant Examiner* — Charles P Coleman
(74) *Attorney, Agent, or Firm* — Wilson Sonsini Goodrich & Rosati

(57) ABSTRACT

A virtual health-care electronic commerce community includes a network to communicate information relating to the community; one or more patients coupled to the network; one or more treating professionals coupled to the network; and a server coupled to the network, the server storing data for each patient and performing patient data visualization in response to a user request.

20 Claims, 14 Drawing Sheets

Related U.S. Application Data continuation of application No. 09/534,461, filed on Mar. 24, 2000, now abandoned.

(51) Int. Cl.
*B33Y 80/00* (2015.01)
*B33Y 50/00* (2015.01)
*G06Q 50/22* (2018.01)
*G06Q 50/24* (2012.01)
*G06F 19/00* (2018.01)

(58) Field of Classification Search
CPC ........ G16H 30/00; G16H 40/00; G16H 50/00; G16H 70/00; G16H 80/00
USPC .................................. 705/2, 3, 20; 702/2, 3
See application file for complete search history.

(56) References Cited

U.S. PATENT DOCUMENTS

| | | |
|---|---|---|
| 3,600,808 A | 8/1971 | Reeve |
| 3,660,900 A | 5/1972 | Andrews |
| 3,683,502 A | 8/1972 | Wallshein |
| 3,738,005 A | 6/1973 | Cohen |
| 3,860,803 A | 1/1975 | Levine |
| 3,916,526 A | 11/1975 | Schudy |
| 3,922,786 A | 12/1975 | Lavin |
| 3,950,851 A | 4/1976 | Bergersen |
| 3,983,628 A | 10/1976 | Acevedo |
| 4,014,096 A | 3/1977 | Dellinger |
| 4,195,046 A | 3/1980 | Kesling |
| 4,253,828 A | 3/1981 | Coles et al. |
| 4,324,546 A | 4/1982 | Heitlinger et al. |
| 4,324,547 A | 4/1982 | Arcan et al. |
| 4,348,178 A | 9/1982 | Kurz |
| 4,478,580 A | 10/1984 | Barrut |
| 4,500,294 A | 2/1985 | Lewis |
| 4,504,225 A | 3/1985 | Yoshii |
| 4,505,673 A | 3/1985 | Yoshii |
| 4,526,540 A | 7/1985 | Dellinger |
| 4,575,330 A | 3/1986 | Hull |
| 4,575,805 A | 3/1986 | Moermann et al. |
| 4,591,341 A | 5/1986 | Andrews |
| 4,609,349 A | 9/1986 | Cain |
| 4,611,288 A | 9/1986 | Duret et al. |
| 4,656,860 A | 4/1987 | Orthuber et al. |
| 4,663,720 A | 5/1987 | Duret et al. |
| 4,664,626 A | 5/1987 | Kesling |
| 4,676,747 A | 6/1987 | Kesling |
| 4,742,464 A | 5/1988 | Duret et al. |
| 4,755,139 A | 7/1988 | Abbatte et al. |
| 4,763,791 A | 8/1988 | Halverson et al. |
| 4,793,803 A | 12/1988 | Martz |
| 4,798,534 A | 1/1989 | Breads |
| 4,836,778 A | 6/1989 | Baumrind et al. |
| 4,837,732 A | 6/1989 | Brandestini et al. |
| 4,850,864 A | 7/1989 | Diamond |
| 4,850,865 A | 7/1989 | Napolitano |
| 4,856,991 A | 8/1989 | Breads et al. |
| 4,877,398 A | 10/1989 | Kesling |
| 4,880,380 A | 11/1989 | Martz |
| 4,889,238 A | 12/1989 | Batchelor |
| 4,890,608 A | 1/1990 | Steer |
| 4,935,635 A | 6/1990 | O'Harra |
| 4,936,862 A | 6/1990 | Walker et al. |
| 4,937,928 A | 7/1990 | van der Zel |
| 4,941,826 A | 7/1990 | Loran et al. |
| 4,964,770 A | 10/1990 | Steinbichler et al. |
| 4,975,052 A | 12/1990 | Spencer et al. |
| 4,983,334 A | 1/1991 | Adell |
| 5,005,126 A | 4/1991 | Haskin |
| 5,011,405 A | 4/1991 | Lemchen |
| 5,017,133 A | 5/1991 | Miura |
| 5,027,281 A | 6/1991 | Rekow et al. |
| 5,035,613 A | 7/1991 | Breads et al. |
| 5,053,883 A | 10/1991 | Johnson |
| 5,055,039 A | 10/1991 | Abbatte et al. |
| 5,059,118 A | 10/1991 | Breads et al. |
| 5,100,316 A | 3/1992 | Wildman |
| 5,121,333 A | 6/1992 | Riley et al. |
| 5,125,832 A | 6/1992 | Kesling |
| 5,128,870 A | 7/1992 | Erdman et al. |
| 5,130,064 A | 7/1992 | Smalley |
| 5,131,843 A | 7/1992 | Hilgers et al. |
| 5,131,844 A | 7/1992 | Marinaccio et al. |
| 5,139,419 A | 8/1992 | Andreiko et al. |
| 5,145,364 A | 9/1992 | Martz et al. |
| 5,176,517 A | 1/1993 | Truax |
| 5,184,306 A | 2/1993 | Erdman et al. |
| 5,186,623 A | 2/1993 | Breads et al. |
| 5,257,203 A | 10/1993 | Riley et al. |
| 5,273,429 A | 12/1993 | Rekow et al. |
| 5,278,756 A | 1/1994 | Lemchen et al. |
| 5,328,362 A | 7/1994 | Watson et al. |
| 5,338,198 A | 8/1994 | Wu et al. |
| 5,340,309 A | 8/1994 | Robertson |
| 5,342,202 A | 8/1994 | Deshayes |
| 5,368,478 A | 11/1994 | Andreiko et al. |
| 5,382,164 A | 1/1995 | Stern |
| 5,395,238 A | 3/1995 | Andreiko et al. |
| 5,440,326 A | 8/1995 | Quinn |
| 5,440,496 A | 8/1995 | Andersson et al. |
| 5,447,432 A | 9/1995 | Andreiko et al. |
| 5,452,219 A | 9/1995 | Dehoff et al. |
| 5,454,717 A | 10/1995 | Andreiko et al. |
| 5,456,600 A | 10/1995 | Andreiko et al. |
| 5,431,562 A | 11/1995 | Andreiko et al. |
| 5,474,448 A | 12/1995 | Andreiko et al. |
| RE35,169 E | 3/1996 | Lemchen et al. |
| 5,518,397 A | 5/1996 | Andreiko et al. |
| 5,528,735 A | 6/1996 | Strasnick et al. |
| 5,533,895 A | 7/1996 | Andreiko et al. |
| 5,542,842 A | 8/1996 | Andreiko et al. |
| 5,549,476 A | 8/1996 | Stern |
| 5,562,448 A | 10/1996 | Mushabac |
| 5,587,912 A | 12/1996 | Andersson et al. |
| 5,590,248 A | 12/1996 | Zarge et al. |
| 5,605,459 A | 2/1997 | Kuroda et al. |
| 5,607,305 A | 3/1997 | Andersson et al. |
| 5,614,075 A | 3/1997 | Andre |
| 5,621,648 A | 4/1997 | Crump |
| 5,645,420 A | 7/1997 | Bergersen |
| 5,645,421 A | 7/1997 | Slootsky |
| 5,655,653 A | 8/1997 | Chester |
| 5,683,243 A * | 11/1997 | Andreiko et al. ................ 433/3 |
| 5,692,894 A | 12/1997 | Schwartz et al. |
| 5,725,376 A | 3/1998 | Poirier |
| 5,725,378 A | 3/1998 | Wang |
| 5,733,126 A | 3/1998 | Andersson et al. |
| 5,740,267 A | 4/1998 | Echerer et al. |
| 5,742,700 A | 4/1998 | Yoon et al. |
| 5,799,100 A | 8/1998 | Clarke et al. |
| 5,800,174 A | 9/1998 | Andersson |
| 5,823,778 A | 10/1998 | Schmitt et al. |
| 5,848,115 A | 12/1998 | Little et al. |
| 5,851,115 A | 12/1998 | Carlsson et al. |
| 5,857,853 A | 1/1999 | van Nifterick et al. |
| 5,866,058 A | 2/1999 | Batchelder et al. |
| 5,879,158 A | 3/1999 | Doyle et al. |
| 5,880,961 A | 3/1999 | Crump |
| 5,880,962 A | 3/1999 | Andersson et al. |
| 5,934,288 A | 8/1999 | Avila et al. |
| 5,957,686 A | 9/1999 | Anthony |
| 5,964,587 A | 10/1999 | Sato |
| 5,971,754 A | 10/1999 | Sondhi et al. |
| 5,975,893 A | 11/1999 | Chishti et al. |
| 5,995,138 A | 11/1999 | Beer et al. |
| 6,015,289 A | 1/2000 | Andreiko et al. |
| 6,044,170 A | 3/2000 | Migdal et al. |
| 6,044,309 A | 3/2000 | Honda |
| 6,049,743 A | 4/2000 | Baba |
| 6,062,861 A | 5/2000 | Andersson |
| 6,068,482 A | 5/2000 | Snow |
| 6,089,868 A | 7/2000 | Jordan et al. |

(56) References Cited

U.S. PATENT DOCUMENTS

| | | | |
|---|---|---|---|
| 6,091,982 A | 7/2000 | Reinke et al. | |
| 6,099,314 A | 8/2000 | Kopelman et al. | |
| 6,123,544 A | 9/2000 | Cleary | |
| 6,152,731 A | 11/2000 | Jordan et al. | |
| 6,183,248 B1 | 2/2001 | Chishti et al. | |
| 6,190,165 B1 | 2/2001 | Andreiko et al. | |
| 6,205,243 B1 | 3/2001 | Migdal et al. | |
| 6,210,162 B1 | 4/2001 | Chishti et al. | |
| 6,217,325 B1 | 4/2001 | Chishti et al. | |
| 6,217,334 B1 | 4/2001 | Hultgren | |
| 6,227,850 B1 | 5/2001 | Chishti et al. | |
| 6,244,861 B1 | 6/2001 | Andreiko et al. | |
| 6,250,918 B1* | 6/2001 | Sachdeva et al. | 433/24 |
| 6,261,248 B1 | 7/2001 | Takaishi et al. | |
| 6,283,761 B1* | 9/2001 | Joao | 434/236 |
| 6,309,215 B1 | 10/2001 | Phan et al. | |
| 6,315,553 B1 | 11/2001 | Sachdeva et al. | |
| 6,318,994 B1 | 11/2001 | Chishti et al. | |
| 6,322,359 B1 | 11/2001 | Jordan et al. | |
| 6,350,119 B1 | 2/2002 | Jordan et al. | |
| 6,350,120 B1 | 2/2002 | Sachdeva et al. | |
| 6,371,761 B1 | 4/2002 | Cheang et al. | |
| 6,382,975 B1 | 5/2002 | Poirier | |
| 6,398,548 B1 | 6/2002 | Muhammad et al. | |
| 6,402,707 B1 | 6/2002 | Ernst | |
| 6,422,864 B1 | 7/2002 | Glatt | |
| 6,431,870 B1 | 8/2002 | Sachdeva | |
| 6,463,344 B1 | 10/2002 | Pavlovskaia et al. | |
| 6,464,496 B1 | 10/2002 | Sachdeva et al. | |
| 6,471,512 B1 | 10/2002 | Sachdeva et al. | |
| 6,482,298 B1 | 11/2002 | Bhatnagar | |
| 6,524,101 B1 | 2/2003 | Phan et al. | |
| 6,540,512 B1 | 4/2003 | Sachdeva et al. | |
| 6,554,611 B2 | 4/2003 | Chishti et al. | |
| 6,572,372 B1 | 6/2003 | Phan et al. | |
| 6,575,751 B1 | 6/2003 | Lehmann et al. | |
| 6,587,828 B1* | 7/2003 | Sachdeva | 705/3 |
| 6,616,444 B2 | 9/2003 | Andreiko et al. | |
| 6,629,840 B2 | 10/2003 | Chishti et al. | |
| 6,632,089 B2 | 10/2003 | Rubbert et al. | |
| 6,633,789 B1 | 10/2003 | Nikolskiy et al. | |
| 6,705,863 B2 | 3/2004 | Phan et al. | |
| 6,722,880 B2 | 4/2004 | Chishti et al. | |
| 6,757,898 B1 | 6/2004 | Ilsen et al. | |
| 6,776,614 B2 | 8/2004 | Wiechmann et al. | |
| 7,027,642 B2 | 4/2006 | Rubbert et al. | |
| 7,107,226 B1 | 9/2006 | Cassidy et al. | |
| 7,156,655 B2 | 1/2007 | Sachdeva et al. | |
| 2002/0006597 A1 | 1/2002 | Andreiko et al. | |
| 2002/0025503 A1* | 2/2002 | Chapoulaud | A61C 7/00 433/24 |
| 2002/0042038 A1 | 4/2002 | Miller et al. | |
| 2002/0048741 A1 | 4/2002 | Jordan et al. | |
| 2002/0156652 A1* | 10/2002 | Sachdeva et al. | 705/2 |
| 2003/0009252 A1 | 1/2003 | Pavlovskaia et al. | |
| 2003/0139834 A1 | 7/2003 | Nikolskiy et al. | |
| 2003/0224311 A1 | 12/2003 | Cronauer | |
| 2004/0002873 A1* | 1/2004 | Sachdeva | 705/2 |
| 2004/0073417 A1* | 4/2004 | Rubbert et al. | 703/11 |
| 2004/0128010 A1 | 7/2004 | Pavlovskaia et al. | |
| 2005/0055118 A1 | 3/2005 | Nikolskiy et al. | |
| 2005/0084826 A1 | 4/2005 | Pilaro et al. | |
| 2005/0159986 A1 | 7/2005 | Breeland et al. | |

FOREIGN PATENT DOCUMENTS

| | | |
|---|---|---|
| AU | 5598894 | 6/1994 |
| CA | 1121955 | 4/1982 |
| DE | 2749802 | 5/1978 |
| DE | 69327661 | 7/2000 |
| EP | 0091876 | 10/1983 |
| EP | 0299490 | 1/1989 |
| EP | 0376873 | 7/1990 |
| EP | 0490848 | 6/1992 |
| EP | 0541500 | 5/1993 |
| EP | 0667753 | 8/1995 |
| EP | 0731673 | 9/1996 |
| EP | 0774933 | 5/1997 |
| ES | 463897 | 1/1980 |
| FR | 2369828 | 6/1978 |
| FR | 2652256 | 3/1991 |
| GB | 1550777 | 8/1979 |
| JP | 53-058191 | 5/1978 |
| JP | 04-028359 | 1/1992 |
| JP | 08-508174 | 9/1996 |
| WO | WO 90/08512 | 8/1990 |
| WO | WO 91/04713 | 4/1991 |
| WO | WO 94/10935 | 5/1994 |
| WO | WO 98/32394 | 7/1998 |
| WO | WO 98/44865 | 10/1998 |
| WO | WO 98/58596 | 12/1998 |
| WO | WO 01/47405 | 7/2001 |
| WO | WO 98/15227 | 7/2001 |

OTHER PUBLICATIONS

"Important Tip About Wearing the Red White & Blue Active Clear Retainer System," Allesee Orthodontic Appliances-Pro Lab, 1 page.
"Inside the ADA," *JADA*, 118:286-294 (Mar. 1989).
"The Choice Is Clear: Red, White & Blue . . . The Simple, Affordable, No-Braces Treatment," Allesee Orthodontic Appliances-Pro Lab product information for doctors, <http://ormco.com/aoa/appliancesservices/RWB/doctor.html>, 5 pages (May 19, 2003).
"The Choice is Clear: Red, White & Blue . . . The Simple, Affordable, No-Braces Treatment," Allesee Orthodontic Appliances-Pro Lab product information for patients, <http://ormco.com/aoa/appliancesservices/RWB/patients.html>, 2 pages (May 19, 2003).
"The Choice Is Clear: Red, White & Blue . . . The Simple, Affordable, No-Braces Treatment," Allesee Orthodontic Appliances-Pro Lab product information, 6 pages (2003).
"The Red, White & Blue Way to Improve Your Smile!" Allesee Orthodontic Appliances-Pro Lab product information for patients, 2 pages.
"You May Be a Candidate for this Invisible No-Braces Treatment," Allesee Orthodontic Appliances-Pro Lab product information for patients, 2 pages.
Alexander et al., "The DigiGraph Work Station Part 2 Clinical Management," *JCO*, pp. 402-407 (Jul. 1990).
Altschuler et al., "Measuring Surfaces Space-Coded by a Laser-Projected Dot Matrix," *SPIE Imaging Applications for Automated Industrial Inspection and Assembly*, vol. 182, p. 187-191 (1979).
Altschuler et al., "Analysis of 3-D Data for Comparative 3-D Serial Growth Pattern Studies of Oral-Facial Structures," AADR Abstracts, Program and Abstracts of Papers, 57th General Session, IADR Annual Session, Mar. 29, 1979-Apr. 1, 1979, New Orleans Marriot, *Journal of Dental Research*, vol. 58, Jan. 1979, Special Issue A, p. 221.
Altschuler et al., "Laser Electro-Optic System for Rapid Three-Dimensional (3D) Topographic Mapping of Surfaces," *Optical Engineering*, 20(6):953-961 (1981).
Altschuler, "3D Mapping of Maxillo-Facial Prosthesis," AADR Abstract #607, 2 pages total, (1980).
American Association for Dental Research, Summary of Activities, Mar. 20-23, 1980, Los Angeles, CA, p. 195.
Andersson et al., "Clinical Results with Titanium Crowns Fabricated with Machine Duplication and Spark Erosion," *Acta. Odontol. Scand.*, 47:279-286 (1989).
Andrews, *The Six Keys to Optimal Occlusion Straight Wire*, Chapter 3, pp. 13-24.
Bartels, et al., *An Introduction to Splines for Use in Computer Graphics and Geometric Modeling*, Morgan Kaufmann Publishers, pp. 422-425 (1987).
Baumrind et al., "A Stereophotogrammetric System for the Detection of Prosthesis Loosening in Total Hip Arthroplasty," NATO Symposium on Applications of Human Biostereometrics, Jul. 9-13, 1978, *SPIE*, vol. 166, pp. 112-123.
Baumrind et al., "Mapping the Skull in 3-D," reprinted from *J. Calif. Dent. Assoc.*, 48(2), 11 pages total, (1972 Fall Issue).

(56) References Cited

OTHER PUBLICATIONS

Baumrind, "A System for Craniofacial Mapping Through the Integration of Data from Stereo X-Ray Films and Stereo Photographs," an invited paper submitted to the 1975 American Society of Photogram Symposium on Close-Range Photogram Systems, University of Ill., Aug. 26-30, 1975, pp. 142-166.
Baumrind, "Integrated Three-Dimensional Craniofacial Mapping: Background, Principles, and Perspectives," *Semin. in Orthod.*, 7(4):223-232 (Dec. 2001).
Begole et al., "A Computer System for the Analysis of Dental Casts," *The Angle Orthod.*, 51(3):253-259 (Jul. 1981).
Bernard et al.,"Computerized Diagnosis in Orthodontics for Epidemiological Studies: A Progress Report," Abstract, *J. Dental Res. Special Issue*, vol. 67, p. 169, paper presented at International Association for Dental Research 66th General Session, Mar. 9-13, 1988, Montreal, Canada.
Bhatia et al., "A Computer-Aided Design for Orthognathic Surgery," *Br. J. Oral Maxillofac. Surg.*, 22:237-253 (1984).
Biggerstaff et al., "Computerized Analysis of Occlusion in the Postcanine Dentition," *Am. J. Orthod.*, 61(3): 245-254 (Mar. 1972).
Biggerstaff, "Computerized Diagnostic Setups and Simulations," *Angle Orthod.*, 40(1):28-36 (Jan. 1970).
Biostar Opeation & Training Manual. Great Lakes Orthodontics, Ltd. 199 Fire Tower Drive, Tonawanda, New York. 14150-5890. 20 pages total.
Blu, et al., "Linear interpolation revitalized", *IEEE Trans. Image Proc.*, 13(5):710-719 (May 2004).
Bourke, "Coordinate System Transformation," (Jun. 1996), p. 1, retrieved from the Internet Nov. 5, 2004, URL <http://astronomy.swin.edu.au/~pbourke/projection/coords>.
Boyd et al., "Three Dimensional Diagnosis and Orthodontic Treatment of Complex Malocclusions With the Invisalign Appliance," *Semin. Orthod.*, 7(4):274-293 (Dec. 2001).
Brandestini et al., "Computer Machined Ceramic Inlays: In Vitro Marginal Adaptation," *J. Dent. Res. Special Issue*, Abstracts, vol. 64, p. 208 (1985).
Brook et al., "An Image Analysis System for the Determination of Tooth Dimensions from Study Casts: Comparison with Manual Measurements of Mesio-distal Diameter," *J. Dent. Res.*, 65(3):428-431 (Mar. 1986).
Burstone (interview), "Dr. Charles J. Burstone on the Uses of the Computer in Orthodontic Practice (Part 1)," *J. Clin. Orthod.*, 13(7):442-453 (Jul. 1979).
Burstone (interview), "Dr. Charles J. Burstone on the Uses of the Computer in Orthodontic Practice (Part 2)," *J. Clin. Orthod.*, 13(8):539-551 (Aug. 1979).
Burstone et al., Precision Adjustment of the Transpalatal Lingual Arch: Computer Arch Form Predetermination, *Am, Journal of Orthodontics*, vol. 79, No. 2 (Feb. 1981), pp. 115-133.
Cardinal Industrial Finishes, Powder Coatings information posted at <http://www.cardinalpaint.com> on Aug. 25, 2000, 2 pages.
Carnaghan, "An Alternative to Holograms for the Portrayal of Human Teeth," 4th Int'l. Conf. on Holographic Systems, Components and Applications, Sep. 15, 1993, pp. 228-231.
Chaconas et al., "The DigiGraph Work Station, Part 1, Basic Concepts," *JCO*, pp. 360-367 (Jun. 1990).
Chafetz et al., "Subsidence of the Femoral Prosthesis, A Stereophotogrammetric Evaluation," *Clin. Orthop. Relat. Res.*, No. 201, pp. 60-67 (Dec. 1985).
Chiappone, (1980). Constructing the Gnathologic Setup and Positioner, *J. Clin. Orthod*, vol. 14, pp. 121-133.
Cottingham, (1969). Gnathologic Clear Plastic Positioner, *Am. J. Orthod*, vol. 55, pp. 23-31.
Crawford, "Computers in Dentistry: Part 1: CAD/CAM: The Computer Moves Chairside," "Part 2: F. Duret—A Man With a Vision," "Part 3: The Computer Gives New Vision—Literally," "Part 4: Bytes 'N Bites" The Computer Moves From the Front Desk to the Operatory, *Canadian Dental Journal*, vol. 54(9), pp. 661-666 (1988).
Crawford, "CAD/CAM in the Dental Office: Does It Work?", *Canadian Dental Journal*, vol. 57, No. 2, pp. 121-123 (Feb. 1991).
Crooks, "CAD/CAM Comes to USC," *USC Dentistry*, pp. 14-17 (Spring 1990).
Cureton, Correcting Malaligned Mandibular Incisors with Removable Retainers, *J. Clin. Orthod*, vol. 30, No. 7 (1996) pp. 390-395.
Curry et al., "Integrated Three-Dimensional Craniofacial Mapping at the Craniofacial Research Instrumentation Laboratory/University of the Pacific," *Semin. Orthod.*, 7(4):258-265 (Dec. 2001).
Cutting et al., "Three-Dimensional Computer-Assisted Design of Craniofacial Surgical Procedures: Optimization and Interaction with Cephalometric and CT-Based Models," *Plast. Reconstr. Surg.*, 77(6):877-885 (Jun. 1986).
DCS Dental AG, "The CAD/CAM 'DCS Titan System' for Production of Crowns/Bridges," DSC Production AG, pp. 1-7 (Jan. 1992).
Definition for "Gingiva," Dictionary.com, pp. 1-3, retrieved from the Internet on Nov. 5, 2004, URL <http://reference.com/search/search?q=gingiva>.
Defranco et al., "Three-Dimensional Large Displacement Analysis of Orthodontic Appliances," *J. Biomechanics*, 9:793-801 (1976).
Dental Institute University of Zurich Switzerland, Program for International Symposium on Computer Restorations: State of the Art of the CEREC-Method, May 1991, 2 pages total.
Dentrac Corporation, Dentrac document, pp. 4-13.
Dent-X posted on Sep. 24, 1998 at <http://www.dent-x.com/DentSim.htm>, 6 pages.
Doyle, "Digital Dentistry," *Computer Graphics World*, pp. 50-52, 54 (Oct. 2000).
Doyle, Doctors use CAD/CAM to take the pain out of extensive dental procedures, [online], [retrieved on Sep. 18, 2002]. Retrieved from the Internet <URL: http://cgw.pennnet.com/Articles/Article_Display.cfm?Section=Archives&Subsection=Display&ARTICLE_ID=83518&KEYWORD=digital%20dentistry>.
DuraClear™ product information, Allesee Orthodontic Appliances-Pro Lab, 1 page.
Duret et al, "CAD-CAM in Dentistry," *J. Am. Dent. Assoc.*, 117:715-720 (Nov. 1988).
Duret et al., "CAD/CAM Imaging in Dentistry," *Curr. Opin. Dent.*, 1:150-154 (1991).
Duret, "The Dental CAD/CAM, General Description of the Project," *Hennson International Product Brochure*, 18 pages total, Jan. 1986.
Duret,"Vers Une Prosthese Informatisee," (English translation attached), *Tonus*, vol. 75, pp. 55-57 (Nov. 15, 1985).
Economides, "The Microcomputer in the Orthodontic Office," *JCO*, pp. 767-772 (Nov. 1979).
Elsasser, Some Observations on the History and Uses of the Kesling Positioner, *Am. J. Orthod*. (1950) 36:368-374.
English translation of Japanese Laid-Open Publication No. 63-11148 to inventor T. Ozukuri (Laid-Open on Jan. 18, 1998) pp. 1-7.
Faber et al., "Computerized Interactive Orthodontic Treatment Planning," *Am. J. Orthod.*, 73(1):36-46 (Jan. 1978).
Felton et al., "A Computerized Analysis of the Shape and Stability of Mandibular Arch Form," *Am. J. Orthod. Dentofacial Orthop.*, 92(6):478-483 (Dec. 1987).
Friede et al., "Accuracy of Cephalometric Prediction in Orthognathic Surgery," Abstract of Papers, *J. Dent. Res.*, 70:754-760 (1987).
Füutterling et al., "Automated Finite Element Modeling of a Human Mandible with Dental Implants," WSCG '98—Conference Program, retrieved from the Internet: <http://wscg.zcu.cz/wscg98/papers98/Strasser_98.pdf>, 8 pages.
Gao et al., "3-D element Generation for Multi-Connected Complex Dental and Mandibular Structure," Proc. Int'l. Workshop on Medical Imaging and Augmented Reality, pp. 267-271 (Jun. 12, 2001).
Gim-Alldent Deutschland, "Das DUX System: Die Technik," 2 pages total.
Gottleib et al., "JCO Interviews Dr. James A. McNamura, Jr., on the Frankel Appliance: Part 2: Clinical Management," *J. Clin. Orthod.*, 16(6):390-407 (Jun. 1982).
Grayson, "New Methods for Three Dimensional Analysis of Craniofacial Deformity, Symposium: Computerized Facial Imaging in Oral and Maxiiofacial Surgery," *AAOMS*, 3 pages total, (Sep. 13, 1990).
Guess et al., "Computer Treatment Estimates in Orthodontics and Orthognathic Surgery," *JCO*, pp. 262-328 (Apr. 1989).

(56) References Cited

OTHER PUBLICATIONS

Heaven et al., "Computer-Based Image Analysis of Artificial Root Surface Caries," Abstracts of Papers, *J. Dent. Res.*, 70:528 (Apr. 17-21, 1991).

Highbeam Research, "Simulating Stress Put on Jaw," Tooling & Production [online], Nov. 1996, pp. 1-2, retrieved from the Internet on Nov. 5, 2004, URL <http://static.highbeam.com/t/toolingamp-production/november011996/simulatingstressputonja . . . >.

Hikage, "Integrated Orthodontic Management System for Virtual Three-Dimensional Computer Graphic Simulation and Optical Video Image Database for Diagnosis and Treatment Planning", *Journal of Japan Orthodontic Society*, Feb. 1987, English translation, pp. 1-38, Japanese version, 46(2), pp. 248-269 (60 pages total).

Hoffmann, et al., "Role of Cephalometry for Planning of Jaw Orthopedics and Jaw Surgery Procedures," (Article Summary in English, article in German), *Informatbnen*, pp. 375-396 (Mar. 1991).

Hojjatie et al., "Three-Dimensional Finite Element Analysis of Glass-Ceramic Dental Crowns," *J. Biomech.*, 23(11):1157-1166 (1990).

Huckins, "CAD-CAM Generated Mandibular Model Prototype from MRI Data," *AAOMS*, p. 96 (1999).

"JCO Interviews, Craig Andreiko , DDS, MS on the Elan and Orthos Systems," *JCO*, pp. 459-468 (Aug. 1994).

"JCO Interviews, Dr. Homer W. Phillips on Computers in Orthodontic Practice, Part 2," *JCO*, pp. 819-831 (Dec. 1983).

Jerrold, "The Problem, Electronic Data Transmission and the Law," *AJO-DO*, pp. 478-479 (Apr. 1988).

Jones et al., "An Assessment of the Fit of a Parabolic Curve to Pre- and Post-Treatment Dental Arches," *Br. J. Orthod.*, 16:85-93 (1989).

Kamada et.al., Case Reports on Tooth Positioners Using LTV Vinyl Silicone Rubber, J. Nihon University School of Dentistry (1984) 26(1): 11-29.

Kamada et.al., Construction of Tooth Positioners with LTV Vinyl Silicone Rubber and Some Case Reports, J. Nihon University School of Dentistry (1982) 24(1):1-27.

Kanazawa et al., "Three-Dimensional Measurements of the Occlusal Surfaces of Upper Molars in a Dutch Population," *J. Dent Res.*, 63(11):1298-1301 (Nov. 1984).

Kochanek, "Interpolating Splines with Local Tension, Continuity and Bias Control," *Computer Graphics*, 18(3):33-41 (Jul. 1984).

Kesling et al., The Philosophy of the Tooth Positioning Appliance, *American Journal of Orthodontics and Oral Surgery* (1945) 31:297-304.

Kesling, Coordinating the Predetermined Pattern and Tooth Positioner with Conventional Treatment, *Am. J. Orthod. Oral Surg.* (1946) 32:285-293.

Kleeman et al., The Speed Positioner, *J. Clin. Orthod.* (1996) 30:673-680.

Kunii et al., "Articulation Simulation for an Intelligent Dental Care System," *Displays* 15:181-188 (1994).

Kuroda et al., Three-Dimensional Dental Cast Analyzing System Using Laser Scanning, *Am. J. Orthod. Dentofac. Orthop.* (1996) 110:365-369.

Laurendeau, et al., "A Computer-Vision Technique for the Acquisition and Processing of 3-D Profiles of Dental Imprints: An Application in Orthodontics," *IEEE Transactions on Medical Imaging*, 10(3):453-461 (Sep. 1991).

Leinfelder, et al., "A New Method for Generating Ceramic Restorations: a CAD-CAM System," *J. Am. Dent. Assoc.*, 118(6):703-707 (Jun. 1989).

Manetti, et al., "Computer-Aided Cefalometry and New Mechanics in Orthodontics," (Article Summary in English, article in German), *Fortschr. Kieferorthop.* 44, 370-376 (Nr. 5), 1983.

McCann, "Inside the ADA," *J. Amer. Dent. Assoc.*, 118:286-294 (Mar. 1989).

McNamara et al., "Invisible Retainers," *J. Clin. Orthod.*, pp. 570-578 (Aug. 1985).

McNamara et al., *Orthodontic and Orthopedic Treatment in the Mixed Dentition*, Needham Press, pp. 347-353 (Jan. 1993).

Moermann et al., "Computer Machined Adhesive Porcelain Inlays: Margin Adaptation after Fatigue Stress," IADR Abstract 339, *J. Dent. Res.*, 66(a):763 (1987).

Moles, "Correcting Mild Malalignments—As Easy As One, Two, Three," *AOA/Pro Corner*, vol. 11, No. 1, 2 pages (2002).

Mörmann et al., "Marginale Adaptation von adhäsuven Porzellaninlays in vitro," Separatdruck aus: Schweiz. Mschr. Zahnmed. 95: 1118-1129, 1985.

Nahoum, "The Vacuum Formed Dental Contour Appliance," *N. Y. State Dent. J.*, 30(9):385-390 (Nov. 1964).

Nash, "CEREC CAD/CAM Inlays: Aesthetics and Durability in a Single Appointment," *Dent. Today*, 9(8):20, Oct. 22-23, 1990.

Nishiyama et al., "A New Construction of Tooth Repositioner by LTV Vinyl Silicone Rubber," *J. Nihon Univ. Sch. Dent.*, 19(2):93-102 (1977).

OrthoCad, Summer Newsletter, "Wired in 3D" (Sep. 10, 2001).

Paul et al., "Digital Documentation of Individual Human Jaw and Tooth Forms for Applications in Orthodontics, Oral Surgery and Forensic Medicine" Proc. of the 24th Annual Conf. of the IEEE Industrial Electronics Society (IECON '98), Sep. 4, 1998, pp. 2415-2418.

Pinkham, "Foolish Concept Propels Technology," *Dentist*, 3 pages total, Jan./Feb. 1989.

Pinkham, "Inventor's CAD/CAM May Transform Dentistry," *Dentist*, 3 pages total, Sep. 1990.

Ponitz, "Invisible Retainers," *Am. J. Orthod.*, 59(3):266-272 (Mar. 1971).

PROCERA Research Projects, "PROCERA Research Projects 1993—Abstract Collection," pp. 3-28 (1993).

Proffit et al., *Contemporary Orthodontics*, (Second Ed.), Chapter 15, Mosby Inc., pp. 470-533 (Oct. 1993).

Raintree Essix & ARS Materials, Inc., Raintree Essix, Technical Magazine Table of contents and Essix Appliances, <httpz;// www.essix.com/magazine/default.html> Aug. 13, 1997, 7 pages.

Redmond et al., "Clinical Implications of Digital Orthodontics," *Am. J. Orthod. Dentofacial Orthop.*, 117(2):240-242 (2000).

Rekow et al., "CAD/CAM for Dental Restorations—Some of the Curious Challenges," *IEEE Trans. Biomed. Eng.*, 38(4):344-345 (Apr. 1991).

Rekow et al., "Comparison of Three Data Acquisition Techniques for 3-D Tooth Surface Mapping," *Annual International Conference of the IEEE Engineering in Medicine and Biology Society*, 13(1):344-345 (1991).

Rekow, "A Review of the Developments in Dental CAD/CAM Systems," (contains references to Japanese efforts and content of the papers of particular interest to the clinician are indicated with a one-line summary of their content in the bibliography), *Curr. Opin. Dent.*, 2:25-33 (Jun. 1992).

Rekow, "CAD/CAM in Dentistry: A Historical Perspective and View of the Future," *J. Can. Dent. Assoc.*, 58(4):283, 287-288 (Apr. 1992).

Rekow, "Computer-Aided Design and Manufacturing in Dentistry: A Review of the State of the Art," *J. Prosthet. Dent.*, 58(4):512-516 (Oct. 1987).

Rekow, "Dental CAD-CAM Systems: What is the State of the Art?", *J. Amer. Dent. Assoc.*, 122:43-48 (1991).

Rekow, "Feasibility of an Automated System for Production of Dental Restorations, Ph.D. Thesis," Univ. of Minnesota, 244 pages total, Nov. 1988.

Richmond et al., "The Development of the PAR Index (Peer Assessment Rating): Reliability and Validity," *Eur. J. Orthod.*, 14:125-139 (1992).

Richmond et al., "The Development of a 3D Cast Analysis System," *Br. J. Orthod.*, 13(1):53-54 (Jan. 1986).

Richmond, "Recording the Dental Cast in Three Dimensions," *Am. J. Orthod. Dentofacial Orthop.*, 92(3):199-206 (Sep. 1987).

Rudge, "Dental Arch Analysis: Arch Form, A Review of the Literature," *Eur. J. Orthod.*, 3(4):279-284 (1981).

Sakuda et al., "Integrated Information-Processing System in Clinical Orthodontics: An Approach with Use of a Computer Network System," *Am. J. Orthod. Dentofacial Orthop.*, 101(3): 210-220 (Mar. 1992).

(56) References Cited

OTHER PUBLICATIONS

Schellhas et al., "Three-Dimensional Computed Tomography in Maxillofacial Surgical Planning," *Arch. Otolamgol. Head Neck Surg.*, 114:438-442 (Apr. 1988).
Schroeder et al., Eds. *The Visual Toolkit*, Prentice Hall PTR, New Jersey (1998) Chapters 6, 8 & 9, (pp. 153-210,309-354, and 355-428, respectively).
Shilliday, (1971). Minimizing finishing problems with the mini-positioner, *Am. J. Orthod.* 59:596-599.
Siemens, "CEREC—Computer-Reconstruction," High Tech in der Zahnmedizin, 14 pages total.
Sinclair, "The Readers' Corner," *J. Clin. Orthod.*, 26(6):369-372 (Jun. 1992).
Sirona Dental Systems GmbH, *CEREC 3D*, Manuel utiiisateur, Version 2.0X (in French), 2003,114 pages total.
Stoll et al., "Computer-aided Technologies in Dentistry," (article summary in English, article in German), *Dtsch Zahna'rztl Z* 45, pp. 314-322 (1990).
Sturman, "Interactive Keyframe Animation of 3-D Articulated Models," Proceedings Graphics Interface '84, May-Jun. 1984, pp. 35-40.
Truax L., "Truax Clasp-Less(TM) Appliance System," *Funct. Orthod.*, 9(5):22-4, 26-8 (Sep.-Oct. 1992).
Tru-Tain Orthodontic & Dental Supplies, Product Brochure, Rochester, Minnesota 55902, 16 pages total.
U.S. Department of Commerce, National Technical Information Service, "Automated Crown Replication Using Solid Photography SM," Solid Photography Inc., Melville NY, Oct. 1977, 20 pages total.
U.S. Department of Commerce, National Technical Information Service, "Holodontography: An Introduction to Dental Laser Holography," School of Aerospace Medicine Brooks AFB Tex, Mar. 1973, 37 pages total.
U.S. Appl. No. 60/050,342, filed Jun. 20, 1997, 41 pages total.
Van Der Linden et al., "Three-Dimensional Analysis of Dental Casts by Means of the Optocom," *J. Dent. Res.*, p. 1100 (Jul.-Aug. 1972).
Van Der Linden, "A New Method to Determine Tooth Positions and Dental Arch Dimensions," *J. Dent. Res.*, 51(4):1104 (Jul.-Aug. 1972).
Van Der Zel, "Ceramic-Fused-to-Metal Restorations with a New CAD/CAM System," *Quintessence Int.*, 24(11):769-778 (1993).
Varady et al., "Reverse Engineering of Geometric Models—An Introduction," *Computer-Aided Design*, 29(4):255-268,1997.
Verstreken et al., "An Image-Guided Planning System for Endosseous Oral Implants," *IEEE Trans. Med. Imaging*, 17(5):842-852 (Oct. 1998).
Warunek et al., Physical and Mechanical Properties of Elastomers in Orthodonic Positioners, *Am J. Orthod. Dentofac. Orthop*, vol. 95, No. 5, (May 1989) pp. 399-400.
Warunek et.al., Clinical Use of Silicone Elastomer Appliances, *JCO* (1989) XXIII(10):694-700.
Wells, Application of the Positioner Appliance in Orthodontic Treatment, *Am. J. Orthodont.* (1970) 58:351-366.
Williams, "Dentistry and CAD/CAM: Another French Revolution," *J. Dent. Practice Admin.*, pp. 2-5 (Jan./Mar. 1987).
Williams, "The Switzerland and Minnesota Developments in CAD/CAM," *J. Dent. Practice Admin.*, pp. 50-55 (Apr./Jun. 1987).

Wishan, "New Advances in Personal Computer Applications for Cephalometric Analysis, Growth Prediction, Surgical Treatment Planning and Imaging Processing," Symposium: Computerized Facial Imaging in Oral and Maxilofacial Surgery Presented on Sep. 13, 1999.
WSCG'98—Conference Program, "The Sixth International Conference in Central Europe on Computer Graphics and Visualization '98," Feb. 9-13, 1998, pp. 1-7, retrieved from the Internet on Nov. 5, 2004, URL <http://wscg.zcu.cz/wscg98/wscg98.h>.
Xia et al., "Three-Dimensional Virtual-Reality Surgical Planning and Soft-Tissue Prediction for Orthognathic Surgery," *IEEE Trans. Inf. Technol. Biomed.*, 5(2):97-107 (Jun. 2001).
Yamamoto et al., "Optical Measurement of Dental Cast Profile and Application to Analysis of Three-Dimensional Tooth Movement in Orthodontics," *Front. Med. Biol. Eng.*, 1(2):119-130 (1988).
Yamamoto et al., "Three-Dimensional Measurement of Dental Cast Profiles and Its Applications to Orthodontics," *Conf. Proc. IEEE Eng. Med. Biol. Soc.*, 12(5):2051-2053 (1990).
Yamany et al., "A System for Human Jaw Modeling Using Intra-Oral Images," Proc. of the 20th Annual Conf. of the IEEE Engineering in Medicine and Biology Society, Nov. 1, 1998, vol. 2, pp. 563-566.
Yoshii, "Research on a New Orthodontic Appliance: The Dynamic Positioner (D.P.); I. The D.P. Concept and Implementation of Transparent Silicone Resin (Orthocon)," *Nippon Dental Review*, 452:61-74 (Jun. 1980).
Yoshii, "Research on a New Orthodontic Appliance: The Dynamic Positioner (D.P.); II. The D.P. Manufacturing Procedure and Clinical Applications," *Nippon Dental Review*, 454:107-130 (Aug. 1980).
Yoshii, "Research on a New Orthodontic Appliance: The Dynamic Positioner (D.P.); III.—The General Concept of the D.P. Method and Its Therapeutic Effect, Part 2. Skeletal Reversed Occlusion Case Reports," *Nippon Dental Review*, 458:112-129 (Dec. 1980).
Yoshii, "Research on a New Orthodontic Appliance: The Dynamic Positioner (D.P.); III. The General Concept of the D.P. Method and Its Therapeutic Effect, Part 1, Dental and Functional Reversed Occlusion Case Reports," *Nippon Dental Review*, 457:146-164 (Nov. 1980).
Google patents search. 'dentistry and web browser and viewer and plug in' Sep. 3, 2015. 2 pages.
Office action dated Sep. 11, 2015 for U.S. Appl. No. 11/033,097.
Spallek, et al. Web-based 3D online crown preparation course for dental students. Department of Dental Informatics and Department of Restorative dentistry, Temple University School of Dentistry, Philadelphia, USA, University of Applied science, Germany. Sep. 3, 2015. 5 pages.
Office action dated Jan. 27, 2010 for U.S. Appl. No. 11/033,097.
Office action dated Feb. 26, 2013 for U.S. Appl. No. 11/033,097.
Office action dated Mar. 18, 2015 for U.S. Appl. No. 11/033,097.
Office action dated Apr. 7, 2014 for U.S. Appl. No. 11/033,097.
Office action dated Apr. 18, 2011 for U.S. Appl. No. 11/033,097.
Office action dated Jun. 14, 2012 for U.S. Appl. No. 11/033,097.
Office action dated Jul. 13, 2009 for U.S. Appl. No. 11/033,097.
Office action dated Jul. 24, 2014 for U.S. Appl. No. 11/033,097.
Office action dated Aug. 16, 2010 for U.S. Appl. No. 11/033,097.
Office action dated Sep. 17, 2013 for U.S. Appl. No. 11/033,097.
Office action dated Oct. 8, 2008 for U.S. Appl. No. 11/033,097.

* cited by examiner

| Virtual Invisalign Practice | | | | | | _ □ X |
|---|---|---|---|---|---|---|
| File Edit View Favorite Tools Help | | | | | | |
| | | ⇦ Back | ⇨ Forward | Address | http://test.webbdesign.com/align_vip/case%20summary/case | Go | invisalign®
Back to Home
Start a New Case

CASE SUMMARY
☐ Action Required (10)
    ClinCheck Awaiting Approval (10)
☐ No Action Required (12)
    Treatment Form Submitted to Align (1)
    Case Received and Under Review (3)
    Order Accepted by Align (2)
    ClinCheck Under Development (2)
    Aligner in Production (2)
    Aligner Shipments Scheduled (2)

Total (22)

NEWS & FEATURES
News From Align
Case Gallery
⊞ Advanced Features
Message Board
⊞ Practice Development
Forms
⊞ Computer

Welcome, Dr. Smile, to your Virtual Invisalign Practice.
This is where you manage your Invisalign practice online. If you don't already have ClinCheck installed on your computer, you can download ClinCheck now.
New to VIP? Click here for a list of VIP's features, or click here for the VIP tour.(posted 4/16/01)
New! Reproximation and Attachment forms are now available for you to view online! Click here for details.(posted 7/27/01)
New! Help Invisalign develop a new feature for Invisalign doctors! Click here for details.(posted 7/23/01)
New! Office staff members around the country can now share their Invisalign experience and best practices. Click here to link to the Invisalign specialist message board.(posted 7/18/01)
New! Click here for important information regarding Invisalign orthodontics. (posted 7/12/01)
New! Not sure if the patient is your Invisalign candidate? Submit a case for screening! Click here for details. (posted 6/28/01)
New! Earn an online gift certificate each time you submit a case online through VIP! Click here for details. (posted 6/26/01)

CURRENT CASES

| ACTION REQUIRED | | NO ACTION REQUIRED | |
|---|---|---|---|
| Patient Name | Status | Patient Name | Status |
| Sam Allen | ClinCheck Awaiting Approval | Alan Banson | ClinCheck Under Development |
| Gary Brown | ClinCheck Awaiting Approval | Amy Charles | Aligner in Production |
| Rickey Denson | ClinCheck Awaiting Approval | Bobby Randolph | Aligner Shipments Scheduled |
| Vick Duncan | ClinCheck Awaiting Approval | Charles Henderson | Case Received and Under Review |
| Steve Dwayne | ClinCheck Awaiting Approval | Chet Runnells | Order Accepted by Align |
| Michelle Edgar | ClinCheck Awaiting Approval | Cindy Caddy | Aligner in Production |
| Kate Furness | ClinCheck Awaiting Approval | Katie Rodriguez | ClinCheck Under Development |
| Bryce Gunning | ClinCheck Awaiting Approval | Lance Wilson | Order Accepted by Align |
| Roy Jackson | ClinCheck Awaiting Approval | Lloyd Hernandez | Treatment Form Submitted to Align |
| Mary Williams | ClinCheck Awaiting Approval | Pam Lawton | Case Received and Under Review |
| | | Patrick Michaels | Case Received and Under Review |
| | | Terry Johnson | Aligner Shipments Scheduled |

FIG. 11

Virtual Invisalign Practice

File Edit View Favorite Tools Help  ⇐ Back  ⇒ Forward  Address [http://test.webbdesign.com/align_vip/case%20summary/case]  Go invisalign®
Back to Home
Start a New Case

CASE SUMMARY
⊞ Action Required (10)
⊞ No Action Required (12)

Total (22)

NEWS & FEATURES

News From Align (New!)
Case Gallery (New!)
⊞ Advanced
Features (New!)
Message Board (New!)
⊞ Practice
⊞ Development
Forms
⊞ Computer
Support
⊞ TutorialPVS
⊞ Pricing (This will log you out of VIP)
Logout

Treatment Planning Form
Instruction for the web based prescription

This prescription allows you to develop a treatment plan for your patient using a series of logical steps. The questions are designed to help you understand the types of cases that the Invisalign system is capable of treating, as well as the surest way to execute that treatment. The form is intended to guide you through acceptable treatment goals and strategies by comparing your treatment goals to your original diagnosis. Note that some of the questions include information that has been quantized into groups from which you can choose. Other areas permit free form text to be entered. For the most part, all questions must be answered to proceed through the form. The checkboxes or buttons that are "grayed out" are either unavailable, or not permitted at this time

Case Type

☐☐☐☐☐☐☐ ?
Information  Treatment
Diagnosis (A1) Please select which Align Recommendation Treatment case
your patient best represents. (Check one for upper jaw and one for lower jaw)

|  | Upper Jaw | Lower Jaw |
|---|---|---|
| Mild Spacing | ○ | ○ |
| Moderate Spacing | ○ | ○ |
| Mild Crowding | ○ | ○ |
| Moderate Crowding | ○ | ○ |
| Sever Crowding | ○ | ○ |
| This arch to remain untreated | ○ | ○ |

(A2) Please evaluate for any of the following conditions, if they are present.
(Select Yes or No for each item.)

|  | Yes | No |
|---|---|---|
| Extractions or extraction spaces of teeth (other than lower incisors) | ○ | ○ |
| Restorative and prophylactic dental care complete | ○ | ○ |
| Complete eruption of the full permanent dentition | ○ | ○ |

FIG. 12

HEALTH-CARE E-COMMERCE SYSTEMS AND METHODS

CROSS-REFERENCES TO RELATED APPLICATIONS

The present application is a continuation of U.S. patent application Ser. No. 11/271,360, filed Nov. 10, 2005, now U.S. Pat. No. 7,904,307, issued Mar. 8, 2011, which is a continuation of U.S. patent application Ser. No. 09/534,461, filed Mar. 24, 2000, now abandoned, the full disclosure of which is incorporated herein by reference.

BACKGROUND OF THE INVENTION

The Internet has become a significant medium for communication and commerce and has enabled millions of people to share information and conduct business electronically. The unique characteristics of the Internet such as its ability to provide enhanced communication, rich text, and graphic environment provide an ideal support for a wide variety of electronic commerce transactions. For example, a consumer can search, review, and extensively shop a number of competing chains in an instant. As such, consumers benefit by being able to obtain a good price relatively quickly and easily.

On-line retailers also benefit, since these retailers can carry a larger number of products at a lower cost and with greater merchandising flexibility without the physical constraints faced by traditional retailers. Additionally, they can assist the consumer's purchase decision by providing relevant information and enabling consumers to shop at their convenience by remaining open 24 hours a day, seven days a week. Online retailers can also provide personalized services and use direct marketing efforts based on information provided by customers.

As such, the Internet has evolved into a unique sales and marketing channel. The ubiquity and convenience of the Internet makes it ideal for dispensing information on certain topics that traditionally require visits to specialists. For example, certain consumers may be interested in products and services associated with orthodontics and dentofacial orthopedics that specializes in the diagnosis, prevention and treatment of dental and facial irregularities ("malocclusion" or "bad bite"). The orthodontic treatment process typically uses corrective appliances such as braces and/or other fixed or removable appliances to bring the teeth, lips and jaws into proper alignment and to achieve a facial balance. The pervasiveness of the Internet makes it an ideal source for information relating to these products and services.

BRIEF SUMMARY OF THE INVENTION

In one aspect, a virtual health-care electronic commerce community includes a network to communicate information relating to the community; one or more patients coupled to the network; one or more treating professionals coupled to the network; and a server coupled to the network, the server storing data for each patient and performing patient data visualization in response to a user request.

Implementations of the above aspect may include one or more of the following. The treating professional can view one or more of the following patient data visualization over the network: a right buccal view; a left buccal view; a posterior view; an anterior view; a mandibular occlusal view; a maxillary occlusal view; an overjet view; a left distal molar view; a left lingual view; a lingual incisor view; a right lingual view; a right distal molar view; an upper jaw view; and a lower jaw view. The treating professionals can include dentists or orthodontists. One or more partners can be connected to the network. The partners can be a financing partner, a supplier, or a delivery company. The treating professionals can perform office management operations using the server. The office management operations include one or more of the following: patient scheduling, patient accounting, and claim processing. The patients and the treating professionals can access the server using browsers.

In another aspect, a method for performing dental-related electronic commerce includes transmitting teeth data associated a patient from a dental server to a treating professional computer over the Internet upon an authorized request; displaying a three-dimensional computer model of the teeth at the treating professional computer using a browser; allowing a treating professional to manipulate the three-dimensional computer model of the teeth using the browser; transmitting the computer model from the treating professional computer to the server; and generating an appliance to treat the patient based on the computer model of the teeth.

Implementations of the above aspect may include one or more of the following. The system can provide financing options for the patient using one or more financing partners. The system can offer an on-line shop geared to the patient's dental requirements. The system also allows a treating professional to manipulate the three-dimensional computer model of the teeth using the browser further comprises displaying a plurality of dental views.

A treating professional can manipulate the three-dimensional computer model of the teeth using the browser further comprises clicking on a tooth to adjust its position. The system can display x, y and z axis to allow the treating professional to adjust the position of the tooth. Supplemental services can also be offered to the patient, including teeth whitening services.

In another aspect, a server supports a health-care electronic commerce community with one or more patients and one or more service providers. The server includes a processor adapted to communicate with a network; a data storage device coupled to the processor and adapted to store data for each patient; and software to communicate 3D patient data in response to a client request.

Implementations can include one or more of the following. A browser can receive the client request and transmitting the request to the server. The browser can use a viewer plug-in to visualize patient data in 3D. The providers can provide health-care service such as dentistry applications, cosmetic augmentation, hair-care enhancements, liposuction, plastic or reconstructive surgery.

Advantages of the system may include one or more of the following. The system supports a virtual community of dental patients, dentists, specialists such as orthodontists and oral surgeons, financial institutions, benefit providers and the providers of dental equipment or services. For treating professionals, such as dentists and orthodontists, the system provides a one-stop solution for planning patient treatments, managing communication with patients, storing patient records and sharing records with relevant persons outside the doctor's office. The system can act as the repository for the file notes and visual imagery (photographs, x-rays and virtual treatment plans) associated with the course of treatment. The doctors will control access to the centralized patient file. Various tools are provided to support the interpretation of information and the diagnostic process. For example, the system allows the doctors to retrieve, and analyze patient information and to simulate using two and three-dimensional visual imagery of the patient's teeth and other anatomical structures. The system supports visualization of the expected outcome of a particular course of treatment. Working together with the patient these images can enhance the patient's understanding of the benefits of treatment and act as a valuable selling tool for the doctor. The system also provides diagnostic decision-support capabilities such as visualizing the placement of implantations, veneers and crowns before or after a course of treatment to straighten the teeth. The system provides an animated prediction of the suggested treatment that helps the patient and the doctor to visualize the pace of treatment. Using these tools, the doctor can easily and quickly view and/or edit the treatment plan. When doctor and patient choose the final treatment plan the system disseminates aspects of the plan and the relevant patient records to the appropriate members of the virtual community, thus reducing the cost and delay associated with traditional physical shipment of patient information. Aspects of the final treatment plan can be used to generate appliances used in the physical treatment. The information associated with the patient's treatment (visual images, virtual treatment plans, file notes and the like) are digitized and maintained in a central storage facility in a secure manner. Doctors and patients can have access to these files without the need to extract files and models from storage and with reduced risk of records being misplaced.

Administratively, the system allows the office to be managed more efficiently without requiring the treating professional to purchase and maintain special software. The system keeps track of all patients that need to be contacted for an appointment. Scheduling can be done automatically or can be customized to the office's preference and availability of treating professionals and supporting resources. Based on the appointments, the system can electronically mail (email) patients with reminders. Alternatively, the system can print reminder cards that can be mailed to patients reminding them of their appointment. The system can also automatically generate personalized correspondence to patients relating to data collected in the initial exam and treatment recommendations. Moreover, the patient can review the proposed treatment with the treating professional anywhere.

The system also simplifies and streamlines the processing of insurance claims to produce an orderly flow of information. Insurance claims can flow through the treating professional's office from pre-authorization to continuation of treatment with a minimal amount of intervention. The system also provides accounting functions to check out patients, post charges, setup contracts, add comments to ledgers, post payments, adjust ledgers, and display all transactions applied to specific ledgers.

Moreover, the treating professionals can leverage the collective purchasing power of the system by being able to order supplies required by patients directly through the system at a discount. These supplies can be directly shipped to the patients, thus avoiding overhead costs associated with handling the supplies. Further, information reviewed or generated by the treating professionals is provided through a secure on-line connection. Thus, the patient's privacy, as well as the treating professional's sensitive office information, is not compromised.

For patients, the system provides a broad array of dental-care resources that help consumers find answers to their critical dental questions and make informed purchasing decisions. The system also enables people to share their experiences and to support one another in managing their medical conditions. This is done through forums where Internet users with interests and concerns about their dental health can interact with each other, to interact in a community environment and to access content created by others.

The system is convenient to use and provides informative shopping experience through which dental care services and dental-related products can be dispensed. Consumers can access the system using an intuitive, easy-to-use shopping interface that is available 24 hours a day, seven days a week. Consumers can shop quickly and conveniently from anywhere Internet access is available. For example, a customer can store his or her dental history and other relevant dental information, as well as create personalized shopping lists for quick and easy reordering of his or her dental supplies.

BRIEF DESCRIPTION OF THE DRAWINGS

FIG. 11 is an exemplary home page of the web-based interface of the present invention.

FIG. 12 is a Treatment Preference template according to the present invention.

DETAILED DESCRIPTION OF THE INVENTION

Figure 1:
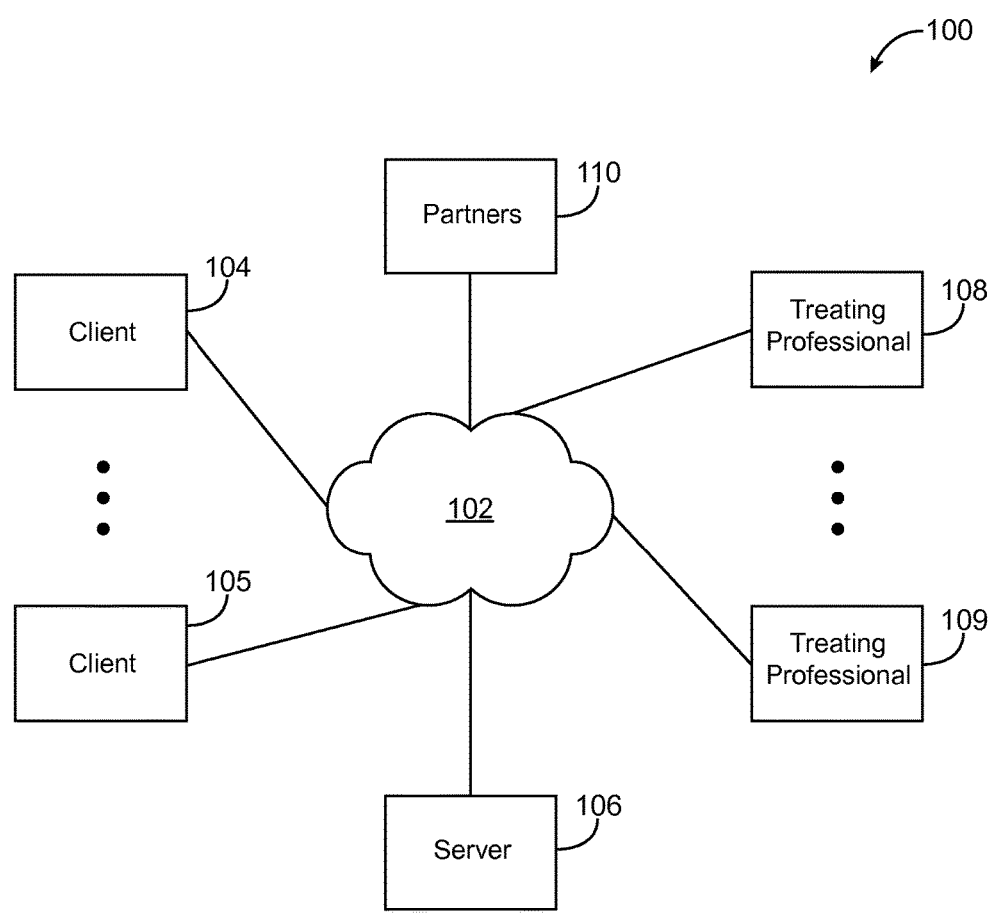
FIG. 1 is a diagram of an exemplary environment supporting electronic commerce.

Referring now to FIG. 1, an environment supporting a dental system 100 is shown. The system 100 communicates over a network 102 that can be a local area network or a wide area network such as the Internet.

One or more client computers 104-105 can be connected to the network 102. In one embodiment where the network 102 is the Internet, the client computers execute a suitable browser such as Navigator from Netscape, Inc. and Internet Explorer from Microsoft Corp. By clicking on the highlighted text (or specific graphic image), the user can jump from the current web page to a new web page address associated with the link—with the new page displayed on the screen. In this manner, the user can "surf the web" by clicking on an almost endless succession of links going to page after page all following a common thread as defined by the text or graphic component of the link label.

Through the network 102, the client computers 104-105 can access a dental server 106. The dental server 106 serves a web site, a portal, a vortal, or a content site for providing dental related information to interested parties such as dental patients, dentists, orthodontists, and others. When sensitive information is communicated through the dental server 106, such information is securely encrypted using Secure Sockets Layer (SSL) technology throughout the transaction. The server 106 can be a stand-alone computer or can be a server farm that can distribute processing and communications activity across a computer network so that no single device is overwhelmed. During load balancing, if one server is swamped with requests, excess requests are forwarded to another server with more capacity.

The network 102 connects the dental server 106 to one or more treating professional workstations 108-109. The workstations 108-109 allow treating professionals access to a plethora of services provided by the dental server 106 such as patient treatment and office management, among others. The dental server 106 stores information associated with patient history on-line in a secure manner. The server 106 also allows the treating professional to have a comprehensive view of the patient's treatment history at any time using a suitable browser, eliminating the need to pull treatment files or charts or to look for misfiled or lost charts. The dental server 106 also provides treating professionals with tools to analyze patient data, for example, tools to reconstruct a 3D model of the teeth. For example, using the browser, the treating professional can request the server 106 to animate the progress of the treatment plan. When the treating professional arrives at a prescription or other final designation, the treatment prescription is used to automatically generate appliances, as described in more details below. Further, in addition to aiding professionals in treating patients, the treating professional can perform office management, purchasing and other logistical operations using the browser and the dental server 106.

In addition to communicating with patients and treating professionals, the dental server 106 can communicate with one or more partners 110 using the network 102. The partners 110 can be product suppliers, service providers, or any suitable commercial entities.

One partner 110 can be a financing partner that offers customers with one or more electronic financing options. In one implementation, the financing partner can be a credit card processing company. The credit card processing company can accept a customer's existing credit card or can issue the customer with a new credit card. Further, the credit card can be issued under the name of a third-party bank, the name of the credit card processing company, or the name of the site supported by the dental server 106 under a co-branding arrangement.

The customer enters the sensitive data such as credit card number, shipping address, among others, onto a purchase form. The credit data is then submitted, collected and passed securely through the dental server 106. This data can be processed in real time or can be collected by mail or telephone and then entered by an operator. A processor at the credit card processing company then verifies that the credit card number is valid and is not stolen, among other anti-fraud measures. If the credit card information is valid, the purchase price will be reserved from the issuing bank of the consumer's credit card and allocated to the account associated with the server 106. Periodically, the credit card processor settles all accounts; it is at this time that all monies move. Funds reserved are transmitted from the issuing bank of the cardholder's credit card to the account of the server 106. Also, discount fees are paid from these funds, as they are moving.

Alternatively, the financing partner can debit from the customer's checking account over the Internet. One such check debiting service is the MerchanTrust™ Paperless Checks™ Services, available from Merchant Commerce, Inc. These services provide customers with the convenience of making online purchases by checking account debits, with no manual data entry required of a merchant. In this embodiment, a customer fills in a form at the site with bank information printed at the bottom of his or her personal check. The information is processed as an Electronic Funds Transfer (EFT) to the customer's account using the Automated Clearinghouse (ACH) payment system.

Yet another possible partner 110 is a dental supply retailer providing an on-line shop on the web site to retail dental products to the customers and treating professionals. The retailer can be a co-branding partner that uses the brand name linked or suitably associated with the web site of the server 106 such that users of the server 106 would not know that the on-line shop is actually operated by a third party. The retailer can offer dental products for brushing, flossing, and cleaning of dental implants and bridges. Other dental products include anti-plaque rinse and plaque-fighting toothpaste. The retailer can also sell other health-care-related products such as prescription drugs; non-prescription drugs; personal care; beauty and spa; vitamins, herbs and nutrition; and medical supplies. Additionally, the retailer can serve the needs of the treating professionals by offering products such as brackets, buccal tubes, bands, archwire products, bonding adhesives, hand instruments, systems, supplies and equipment.

Yet another partner 110 can be a shipping partner. The shipping partner delivers dental supply of goods received from a multiplicity of producers and manufacturers for ultimate distribution to each customer. The facilities for warehousing and introduction of goods into a transportation stream for redistribution are the so-called cross docking facilities. The supply or good flows in bulk from a producer or a manufacturer to one or more cross docking facilities owned by either the shipping partner or the operator of the server 106. The items are then broken into smaller unit sizes and distributed to the customers.

The above list of partners lists only exemplary partners and is not an exhaustive list. Other possible partners include value-added service providers such as third party software providers who provide plug-in viewing and diagnostic enhancements that can be used by the professionals.

The server 106 can perform dynamic targeting and information gathering. The users provide demographic information when they register for our service. The server 106 can track our users' behavior the entire time they are online. As a result, the server 106 can deliver targeted advertisements and measure their effectiveness. For example, users can receive ads from a brokerage firm when they are viewing sites containing stock quotes or financial news, or receive promotions from a bookseller when browsing sites containing book reviews. As such, the dental server 106 can provide a prominent and sustained advertising medium to the community. In contrast to most portal and content sites which display advertising, the site remains with users the entire time they are online. Once users are logged on, the site remains in full view throughout the session, including when they are waiting for pages to download, navigating the Internet and even engaging in non-browsing activities such as sending or receiving e-mail. The constant visibility of the site allows advertisements to be displayed for a specified period of time.

In combination, the dental server 106 forms a hub that links dental clients using client computers 104-105, treating professionals using workstations 108-109, and partners 110 into a living electronic commerce (e-commerce) community.

Figure 2:
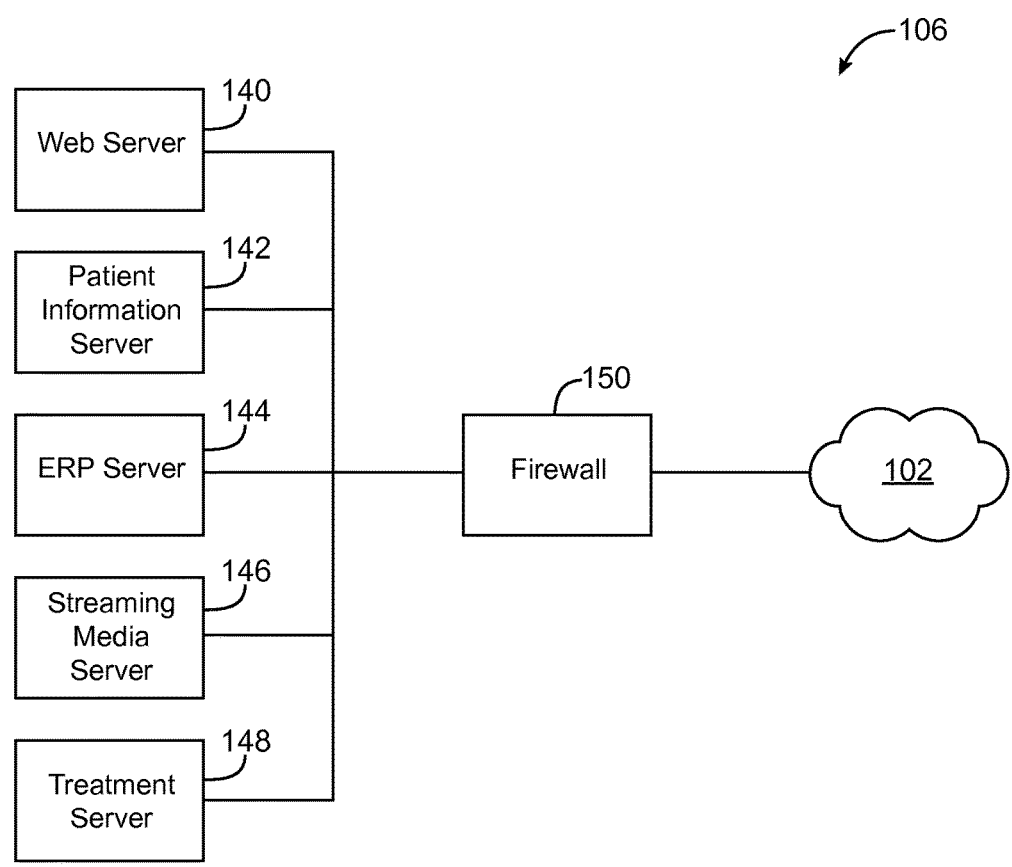
FIG. 2 is a diagram of a server to support electronic commerce.

FIG. 2 shows an embodiment of the server 106. The server 106 includes a web server 140, a patient information server 142, a resource planning (RP) server 144 and a streaming server 146. In one embodiment, the RP server 144 runs Microsoft SQL server and provides information relating to a doctor or a patient such as address and history. When a patient's case or static snapshots of the case is needed, the data is pulled from the patient information server 142. When media data such as video needs to be streamed to a requesting client, the streaming server 146 can send the stream. In one implementation, the streaming data is stored in Quick-Time format on a Linux-based server running the Quick-Time server software.

The servers can be clustered. In one embodiment using Microsoft's Cluster Server, cluster-enabled applications such as Microsoft's SQL Server and Exchange. With Cluster Server, two servers can run applications at the same time. When one server fails, the remaining server handles its application as well as the failed server's applications. Next, the remaining server adopts the IP address of the failed server and mounts one or more data drives that the two systems share. The remaining server is rebooted and applications such as SQL Server can be started and initialized on this server. Persistent clients can re-attach to the server and continue to operate.

Figure 3:
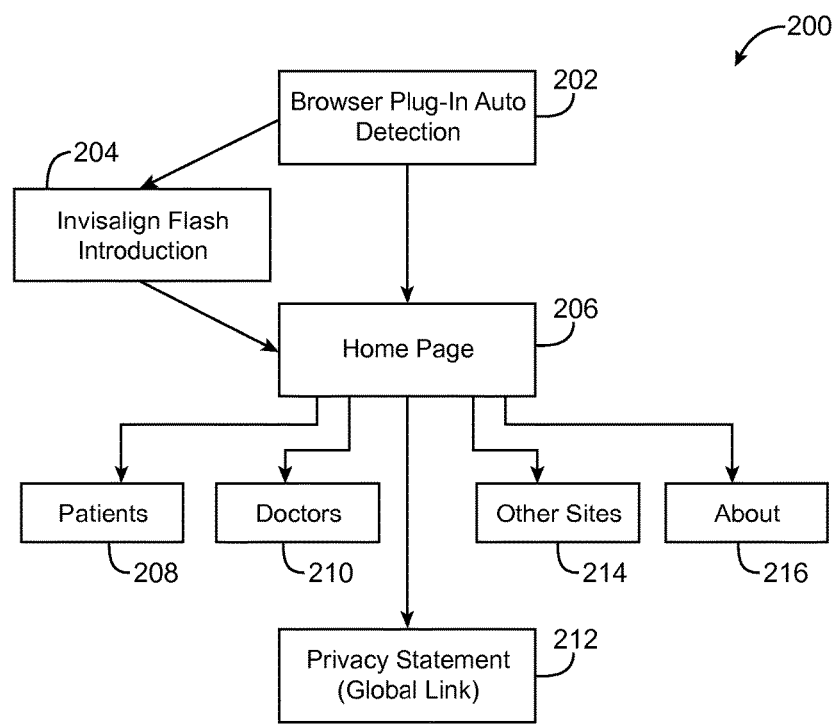
FIG. 3 is a diagram of a web site on the server of FIG. 2.

Referring now to FIG. 3, a diagram 200 shows various major functions supported by the dental server 106. First, the process 200 performs an automatic detection for the existence of a browser welcome plug-in (step 202). If the welcome plug-in exists, an introductory animation (flash) is shown (step 204). From step 204 or 206, the process 200 shows a home page (step 208) with one or more links. A link is created by having a word in a text field (or a graphic image on a web page) linked to the location of another web page, via a string of information setting forth the new web page address presented in hypertext transfer protocol (HTTP), among others.

The user can navigate the home page to join a particular site from a constellation of related sites. For instance, the user can navigate to a patient's site (step 208), a doctor's site (step 210), a privacy statement site (step 212), one or more additional sites (step 214), and an about site (step 216), among others. The additional sites can be an on-line shopping store that is co-branded with the web site hosted by the server 106, or the on-line shopping store can be directly affiliated with a third party such as planet-rx.com, among others. The additional sites can also be third party value-added providers of products and/or services.

Figure 4:
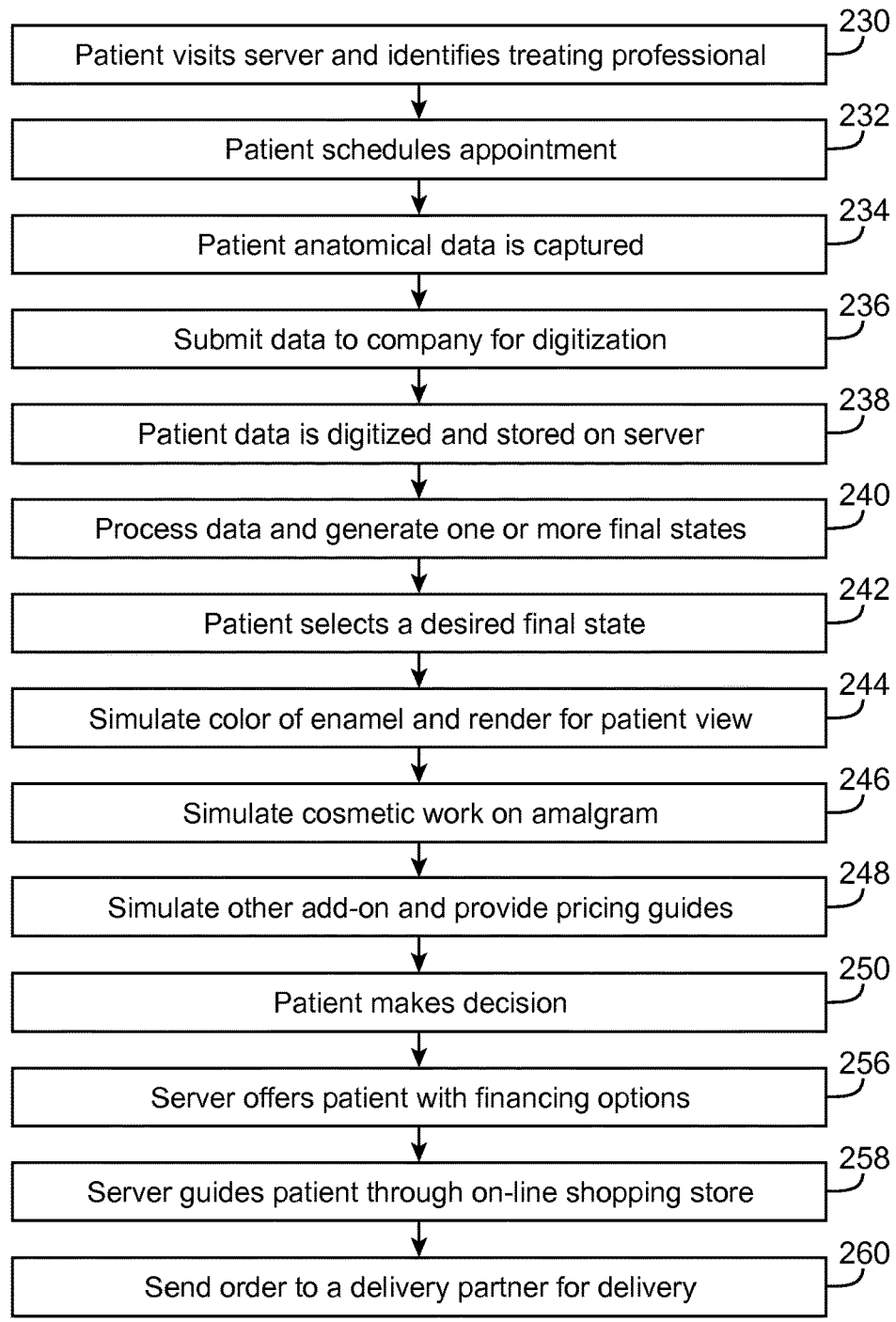
FIG. 4 is a flowchart of a process for selecting dental services from a patient's perspective.
Figure 5:
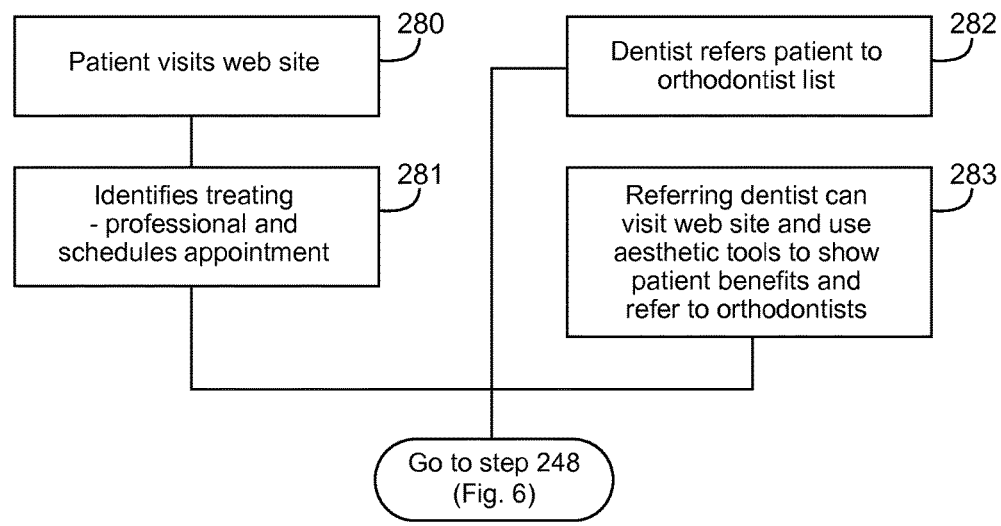
FIG. 5 is a flowchart of a first process for providing dental services from a treating professional's perspective.
Figure 6:
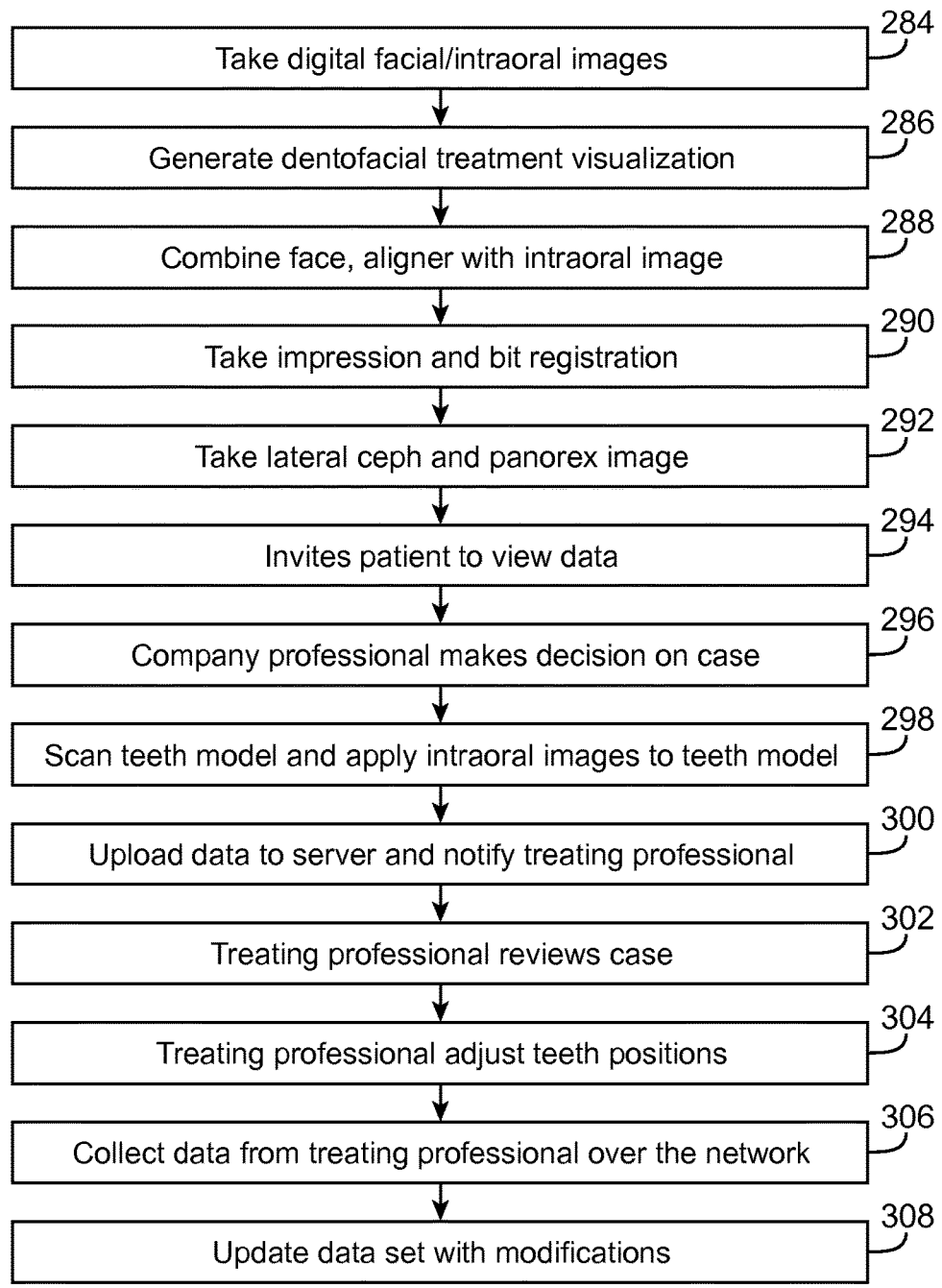
FIG. 6 is a flowchart of a second process for providing dental services from a treating professional's perspective.

FIG. 4 illustrates an exemplary usage of the system of FIG. 1 from a patient's perspective. First, a prospective client using a client computer 104 visits the web site on the dental server 106 and identifies a treating professional meeting one or more criteria, for example a professional whose location is closest to his or her home address (step 230). Next, the patient schedules an appointment with the treating professional (step 232). At the meeting, an assistant captures various anatomical data from the patient by taking digital photographs of the face and teeth, taking x-rays of the front, back, side, and top/bottom of the patient, taking one or more impressions, among others (step 234). Next, this information is entered into a form on the server 106 (step 236). The data is then digitized, stored on the server 106, and made available to the treating professionals and the patient over the Internet (step 238). Next, the server 106 and one or more orthodontic treating persons process the patient data and render the patient's teeth in a plurality of alternative final states (step 240). Based on the choices, the patient selects a desired final state (step 242).

In addition to performing orthodontic operations, the server 106 can also perform other value-added services. For example, processes executed by the server 106 can simulate the color of the patient's enamel and show the color of the teeth before and after bleaching (step 244). Further, processes on the server 106 can simulate the color of the patient's silver fillings (amalgram) and show the teeth after cosmetic work to cover the amalgam (step 246). After visualizing the effects of the operations, comparing the before and after operations, and reviewing guideline pricing for the orthodontic operation as well as add-ons such as bleaching (step 248), the patient makes a decision (step 250).

Once the patient has accepted a particular treatment selection, the server 106 offers the patient with one or more financing options from one of its financial partners (step 256). Additionally, the server 106 can guide the patient to an on-line shopping store to purchase products relating to his or her dental health (step 258). For example, the patient can buy cleaning supplies, brushes, and flossing supply at a price competitive to his or her traditional stores. Moreover, the products can be delivered to the patient using one or more delivery partners at a convenient time (step 260).

FIG. 4 illustrates an exemplary usage of the system of FIG. 1 from a treating professional's perspective. A prospective patient uses a client computer 104 and visits the web site on the dental server 106 (step 280). The client identifies a treating professional and schedules an appointment with the treating professional (step 281). Alternatively, a referring dentist can refer the client to the treating orthodontist (step 282). The referring dentist can visit the web site on the dental server 106 and uses one or more dental esthetic tools to show patients the potential benefits of anterior and posterior esthetic restorations and, if the patient is interested, refers the patient to the treating professional (step 283).

During an initial examination, the treating professional or an assistant takes a set of digital facial and intraoral images which is uploaded to a secure, collaborative workspace on the dental server 106 (step 284). The workspace is shared with the referring dentist.

Next, the treating professional generates a dentofacial treatment visualization showing the patient's face and smile before and after treatment (step 286). The treating professional can also combine the patient's face and an aligner into the intraoral image to show how inconspicuous the appliance will be (step 288).

Once the patient requests treatment, the treating professional takes impressions and a bite registration and sends the information to the company (step 290). The treating professional also takes a lateral ceph and a panorex and uploads them and a treating prescription to the workspace (step 292). The professional's assistant creates a separate workspace for the patient, uploads selected "before and after" images into it, and invites the patient to review the images (step 294).

At the company, another professional reviews the records and decides to accept or decline the case (step 296). The models are then scanned, and the intraoral images are retrieved and used to texture-map enamel and gingiva (step 298). The data is then sent to the workspace and the treating professional is notified (step 300).

In one embodiment, the tooth models may be posted on a hypertext transfer protocol (http) web site for limited access by the corresponding patients and treating clinicians. Since realistic models have a large volume of data, the storage and transmission of the models can be expensive and time consuming. To reduce transmission problems arising from the large size of the 3D model, in one embodiment, data associated with the model is compressed. The compression is done by modeling the teeth meshes as a curve network before transmission to the treating professional. Once the curve network is received, the 3D model is reconstructed from the curve network for the treating professional to analyze. More information on the compression is disclosed in an application having Ser. No. 09/506,419, filed Feb. 17, 2000 (now U.S. Pat. No. 6,463,344), entitled, "EFFICIENT DATA REPRESENTATION OF TEETH MODEL", and filed by ELENA PAVLOVSKAIA and HUAFENG WEN, the contents of which are hereby incorporated.

The treating professional can, at his or her convenience, check the setup, and review the information sent in step 300 (step 302). The treating professionals can use a variety of tools to interpret patient information. For example, the treating professional can retrieve and analyze patient information through a reconstructed 3D model of the patient's teeth and other anatomical structures. The professional can view animations showing the progress of the treatment plan to help the treating physician visualize the pace of treatment. Using these tools, the treating professional can easily and quickly view and/or edit the treatment plan.

If necessary, the treating professional can adjust one or more teeth positions at various intermediate stages of treatment (step 302). A variety of diagnostic decision-support capabilities such as automated teeth collision detection can be used to aid the treating professional in adjusting the teeth positions.

When the treating professional arrives at a prescription or other final designation, the treatment information is automatically collected by the system over the Internet, thus eliminating the cost and delay associated with the traditional physical shipping of patient information (step 304). These modifications are then retrofitted onto the dataset used to generate the aligners (step 306).

Figure 7:
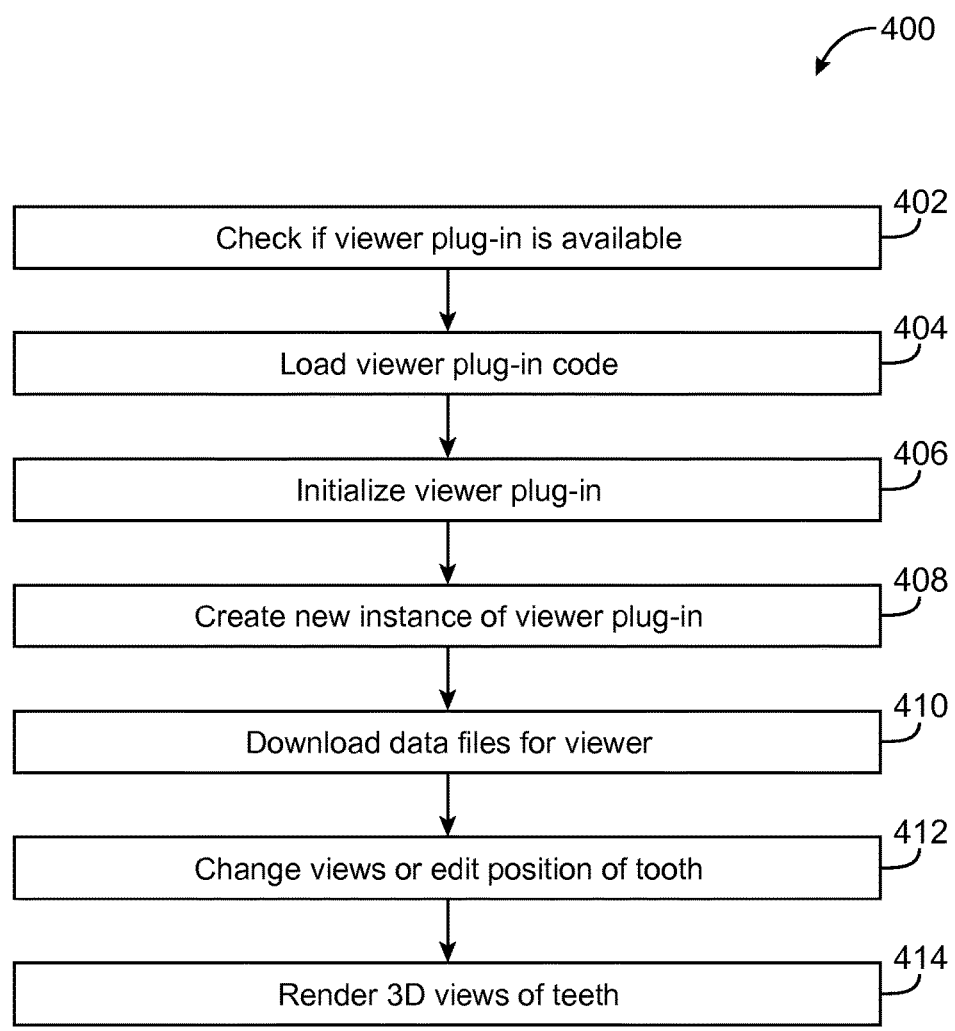
FIG. 7 is a flowchart of a process to render 3D views of a patient's teeth on a browser.
Figure 8:
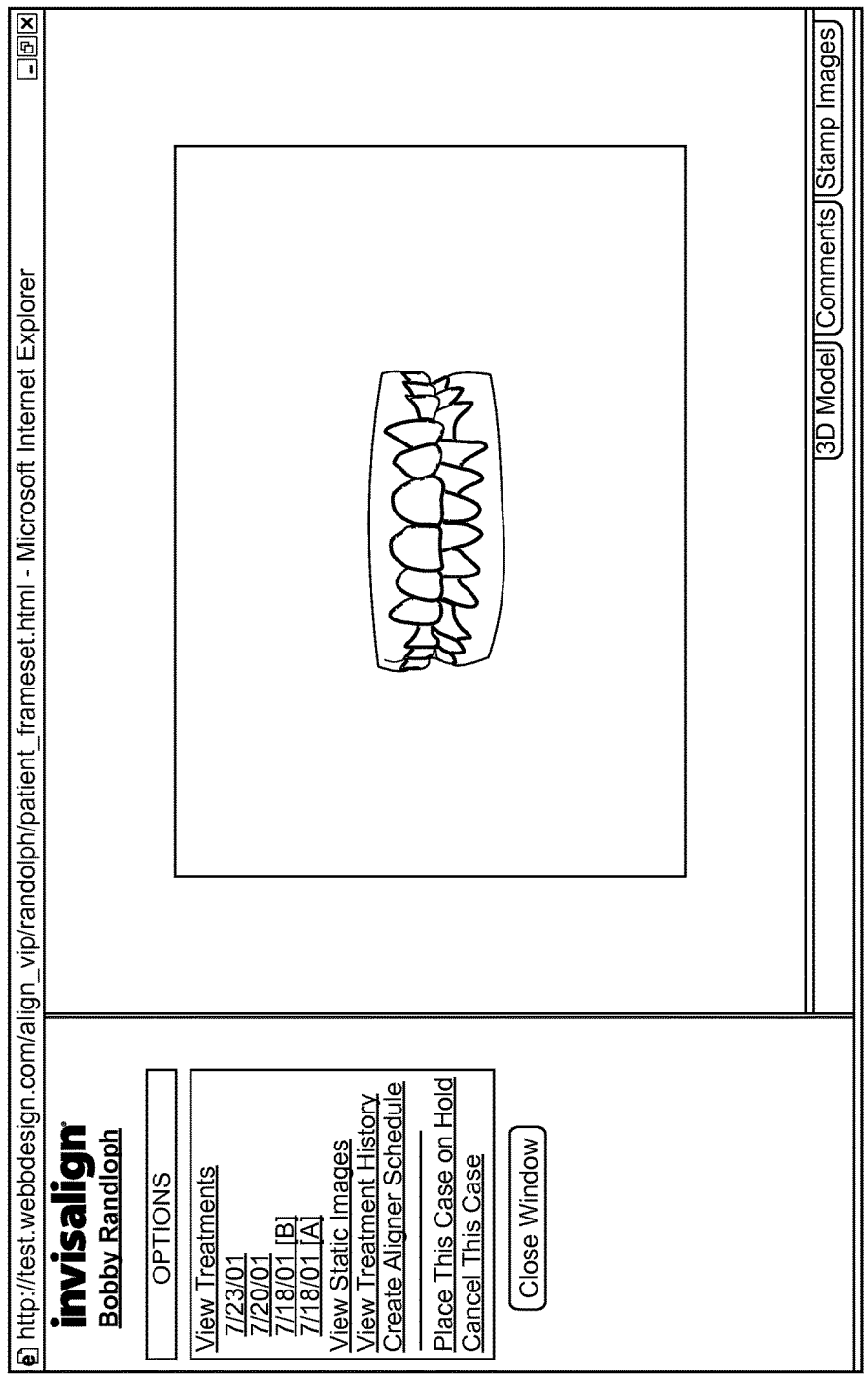
FIG. 8 is an exemplary output of the process of FIG. 7 using the browser.

FIG. 7 shows a process 400 associated with a viewer that allows the treating professional to visualize the patient's teeth over the network 102 such as the Internet. In one embodiment, during start-up, a browser checks for a viewer plug-in module embodying the process 400 in a "plugins" subdirectory (Windows) or Plug-ins folder (Mac OS) in the same folder or directory as the browser (step 402). If the viewer plug-in module is available, the browser looks for a MIME type and extension info from the version resource. Through a TYPE attribute, the browser knows the MIME type and can load a registered plug-in first and, if there are no matches for the MIME type, the browser looks for a helper application.

Once the viewer plug-in is identified, the browser loads the viewer plug-in code into memory (step 404); initializes the viewer plug-in (step 406); and creates a new instance of the viewer plug-in (step 408). When the professional leaves the site or closes the window, the viewer plug-in instance is deleted. When the last instance of the viewer plug-in is deleted, the plug-in code is unloaded from memory.

Next, data files are downloaded to the viewer plug-in (step 410). In one implementation, the viewer plug-in downloads a data file from the dental server 102 using a suitable protocol such as a file transfer protocol (FTP). The viewer plug-in uses the downloaded file to present the treatment plan graphically to the clinician. The viewer plug-in also can be used by the treatment plan designer at the host site to view images of a patient's teeth. FIG. 4 shows an exemplary user interface for the viewer plug-in of FIG. 3. The professional can change views, select a particular tooth and change its position as desired (step 412).

3-D images of various orthodontic views can then be rendered after each instruction from the treating professional is received (step 414). In this process, an origin point, or "look from" point associated with a camera view is generated. Next, a "look at" point or a focus point associated with the camera view is determined. In this system, the line from LookFromPoint to LookAtPoint defines the direction the camera is shooting at. Additionally, a camera Z vector, or up vector, is determined.

Exemplary pseudo code implementations for generating various orthodontic views is shown below. With reference to the pseudo code, the code defines a bounding box of one mold (2 arches) which is the smallest cube containing the molds geometry. Other settings associated with the bounding box include:

Z_Axis: point from lower to upper,

Y_Axis: point from inside mouse to front teeth (incisors)

X Axis: point from center to left.

FieldOfView: is the open angle, it corresponding to lens

HalfFieldOfView: FieldOfView*0.5

MoldCenter: Center of the BoundingBox

X_Length: BoundingBox X dimension

Y_Length: BoundingBox X dimension

Z_Length: BoundingBox X dimension

X_MIN: minimum X value of the BoundingBox, i.e. right most surface cube X value.

X_MAX: maximum X value of the BoundingBox

Y_MIN: minimum Y value of the BoundingBox

Y_MAX: maximum Y value of the BoundingBox

Z_MIN: minimum Z value of the BoundingBox

Z_MAX: maximum Z value of the BoundingBox

---

RIGHT BUCCAL OVERJET VIEW PSEUDO-CODE

```
CameraLookFromPoint:
   X = 0.5 * MoldCenter.X + 0.5 * X_Max + 0.25 *
   MAX(Y_Length, Z_Length)
/ tan(HalfFieldOfView);
   Y = MoldCenter.Y
   Z = MoldCenter.Z − 0.25 * MAX(Y_Length, Z_Length) /
   tan( HalfFieldOf
View);
CameraLookAtPoint:
   X = MoldCenter.X + 0.25 * X_Length;
   Y = MoldCenter.Y;
   Z = MoldCenter.Z;
CameraUpVector:   ZAxis;
```

---

ANTERIOR OVERJET VIEW PSEUDO-CODE

```
CameraLookFromPoint:
   X = MoldCenter.X;
   Y = 0.5 * MoldCenter.Y + 0.5 * Y_Max + 0.25 *
   MAX(X_Length, Z_Length)
/ tan( HalfFieldOfView);
   Z = MoldCenter.Z − 0.25 * MAX(X_Length, Z_Length) /
   tan(HalfFieldOf
View);
CameraLookAtPoint:
   X = MoldCenter.X;
   Y = MoldCenter.Y + 0.25 * Y_Length;
   Z = MoldCenter.Z;
CameraUpVector:   ZAxis;
```

| LEFT BUCCAL OVERJET VIEW PSEUDO-CODE |
|---|
| CameraLookFromPoint:<br>    X = 0.5 * MoldCenter.X + 0.5 * X_Min − 0.25 *<br>    MAX(Y_Length, Z_Length)<br>/ tan( HalfFieldOfView);<br>    Y = MoldCenter.Y;<br>    Z = MoldCenter.Z − 0.25 * MAX(Y_Length, Z_Length) /<br>    tan( HalfFieldOf<br>View);<br>CameraLookAtPoint:<br>    X = MoldCenter.X − 0.25 * X_Length;<br>    Y = MoldCenter.Y;<br>    Z = MoldCenter.Z;<br>CameraUpVector:   ZAxis; |

| LEFT DISTAL_MOLAR |
|---|
| CameraLookFromPoint:<br>    X = MoldCenter.X − 0.25 * X_Length;<br>    Y = Y_Min − 0.25 * MAX(X_Length, Z_Length) /<br>tan( HalfFieldOfView);<br>    Z = MoldCenter.Z;<br>CameraLookAtPoint:<br>    X = MoldCenter.X − 0.25 * X_Length;<br>    Y = MoldCenter.Y;<br>    Z = MoldCenter.Z;<br>CameraUpVector:   ZAxis; |

| LEFT LINGUAL VIEW PSEUDO-CODE |
|---|
| CameraLookFromPoint:<br>    X = MoldCenter.X + 0.125 * X_Length;<br>    Y = MoldCenter.Y;<br>    Z = MoldCenter.Z;<br>CameraLookAtPoint:<br>    X = MoldCenter.X − 0.25 * X_Length;<br>    Y = MoldCenter.Y;<br>    Z = MoldCenter.Z;<br>CameraUpVector:   ZAxis; |

| LINGUAL INCISOR VIEW PSEUDO-CODE |
|---|
| CameraLookFromPoint:<br>    X = MoldCenter.X;<br>    Y = MoldCenter.Y;<br>    Z = MoldCenter.Z;<br>CameraLookAtPoint:<br>    X = MoldCenter.X;<br>    Y = MoldCenter.Y + 0.25 * Y_Length;<br>    Z = MoldCenter.Z;<br>CameraUpVector:   ZAxis; |

| RIGHT LINGUAL VIEW PSEUDO-CODE |
|---|
| CameraLookFromPoint:<br>    X = MoldCenter.X + 0.125 * X_Length;<br>    Y = MoldCenter.Y;<br>    Z = MoldCenter.Z;<br>CameraLookAtPoint:<br>    X = MoldCenter.X + 0.25 * X_Length;<br>    Y = MoldCenter.Y;<br>    Z = MoldCenter.Z<br>CameraUpVector:   ZAxis; |

| RIGHT DISTAL MOLAR VIEW PSEUDO-CODE |
|---|
| CameraLookFromPoint:<br>    X = MoldCenter.X + 0.25 * XLength;<br>    Y = Y_MIN − 0.25 * MAX( X_Length, Z_Length) /<br>    tan(HalfFieldOfView);<br>    Z = MoldCenter.Z;<br>CameraLookAtPoint:<br>    X = MoldCenter.X + 0.25 * X_Length;<br>    Y = MoldCenter.Y;<br>    Z = MoldCenter.Z;<br>CameraUpVector:   ZAxis; |

Figure 9:
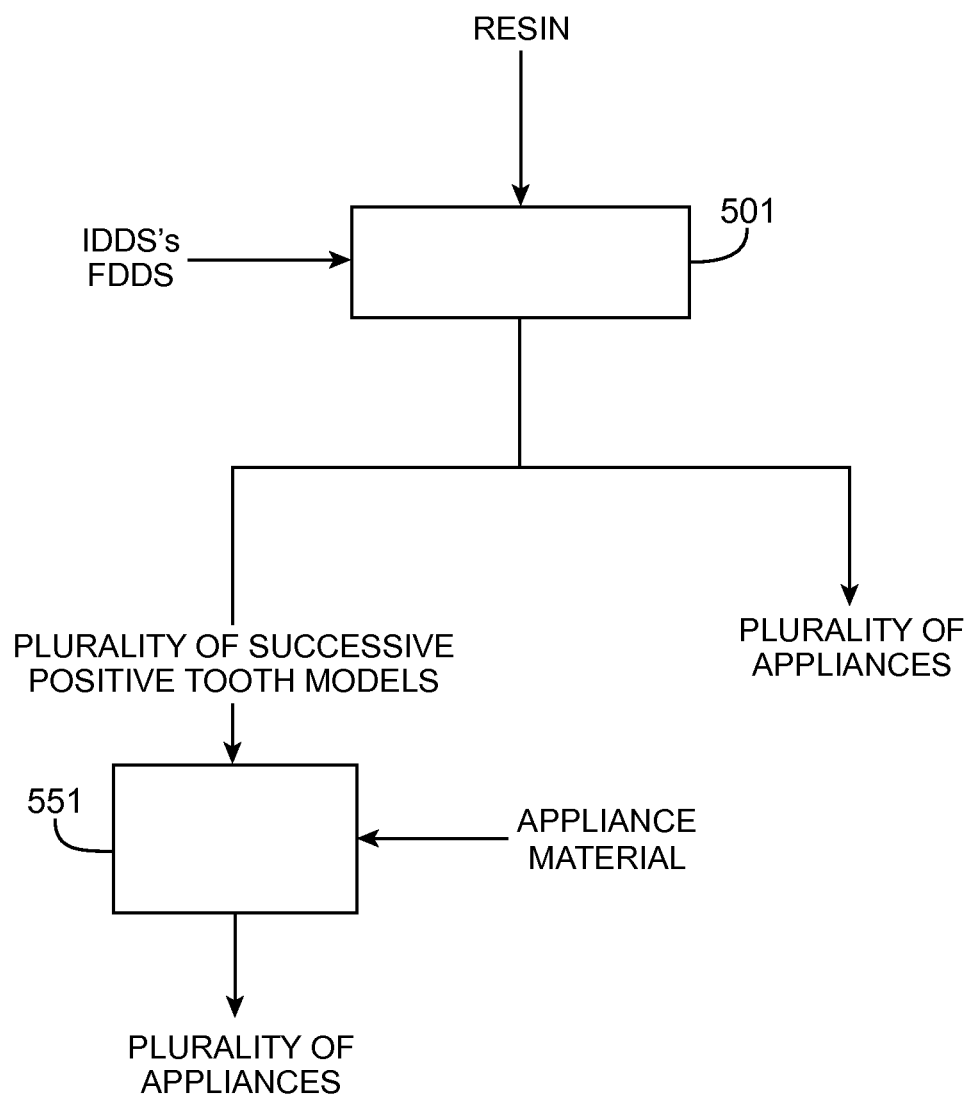
FIG. 9 is a diagram of a system for manufacturing appliances.

Once the intermediate and final data sets have been created, the appliances may be fabricated as illustrated in FIG. 9. Common fabrication methods employ a rapid prototyping device 501 such as a stereolithography machine. A particularly suitable rapid prototyping machine is Model SLA-250/50 available from 3D System, Valencia, Calif. The rapid prototyping machine 501 selectively hardens a liquid or other non-hardened resin into a three-dimensional structure which can be separated from the remaining non-hardened resin, washed, and used either directly as the appliance or indirectly as a mold for producing the appliance. The prototyping machine 501 receives the individual digital data sets and produces one structure corresponding to each of the desired appliances. Generally, because the rapid prototyping machine 501 may utilize a resin having non-optimum mechanical properties and which may not be generally acceptable for patient use, the prototyping machine typically is used to produce molds which are, in effect, positive tooth models of each successive stage of the treatment. After the positive models are prepared, a conventional pressure or vacuum molding machine 551 is used to produce the appliances from a more suitable material, such as 0.03 inch thermal forming dental material, available from Tru-Tain Plastics, Rochester, Minn. 55902. Suitable pressure molding equipment is available under the trade name BIOSTAR from Great Lakes Orthodontics, Ltd., Tonawanda, N.Y. 14150. The molding machine 551 produces each of the appliances directly from the positive tooth model and the desired material. Suitable vacuum molding machines are available from Raintree Essix, Inc.

After production, the appliances can be supplied to the treating professional all at one time. The appliances are marked in some manner, typically by sequential numbering directly on the appliances or on tags, pouches, or other items which are affixed to or which enclose each appliance, to indicate their order of use. Optionally, written instructions may accompany the system which set forth that the patient is to wear the individual appliances in the order marked on the appliances or elsewhere in the packaging. Use of the appliances in such a manner will reposition the patient's teeth progressively toward the final tooth arrangement.

Because a patient's teeth may respond differently than originally expected, the treating clinician may wish to evaluate the patient's progress during the course of treatment. The system can also do this automatically, starting from the newly-measured in-course dentition. If the patient's teeth do not progress as planned, the clinician can revise the treatment plan as necessary to bring the patient's treatment back on course or to design an alternative treatment plan. The clinician may provide comments, oral or written, for use in revising the treatment plan. The clinician also can form another set of plaster castings of the patient's teeth for digital imaging and manipulation. The clinician may wish to limit initial aligner production to only a few aligners, delaying production on subsequent aligners until the patient's progress has been evaluated.

Figure 10:
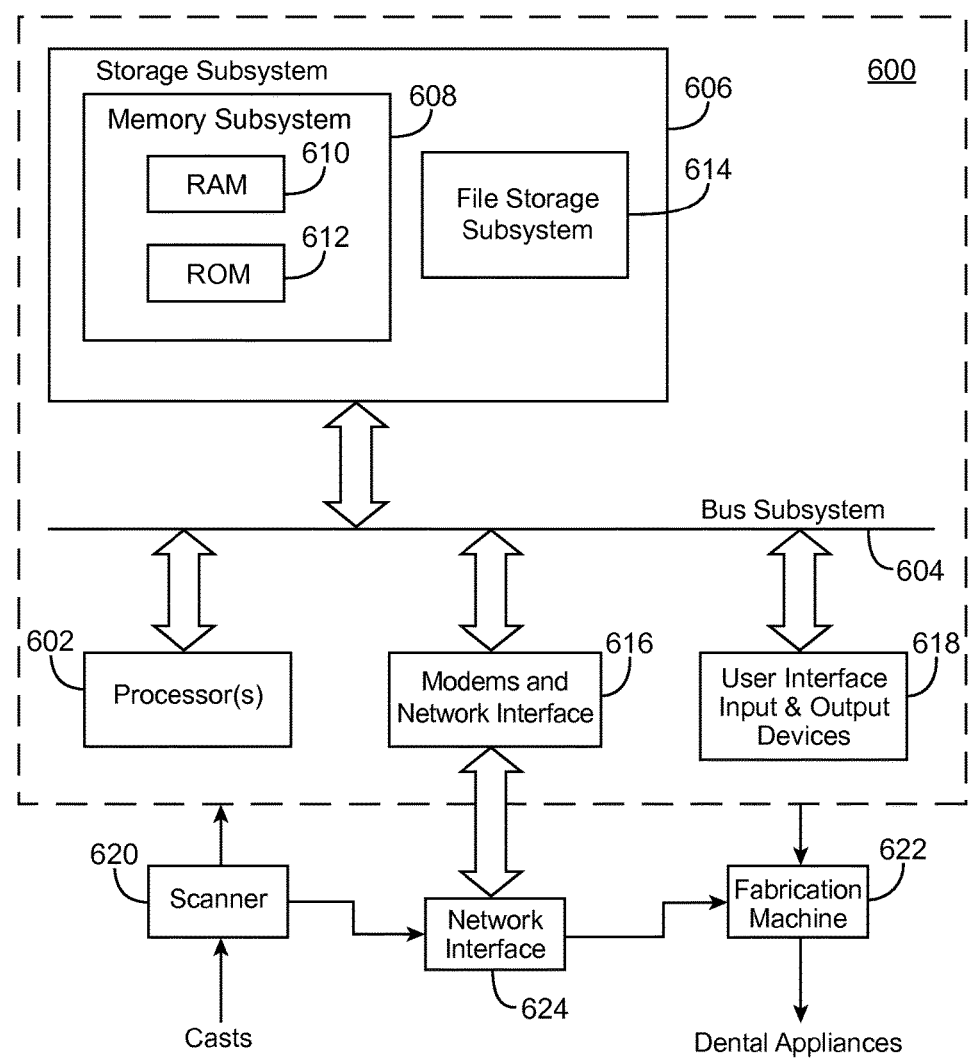
FIG. 10 is a diagram illustrating a computer system to support the fabrication of appliances.

FIG. 10 is a simplified block diagram of a data processing system 600 that may be used to develop orthodontic treatment plans. The data processing system 600 typically includes at least one processor 602 that communicates with a number of peripheral devices via bus subsystem 604. These peripheral devices typically include a storage subsystem 606 (memory subsystem 608 and file storage subsystem 614), a set of user interface input and output devices 618, and an interface to outside networks 616, including the public switched telephone network. This interface is shown schematically as "Modems and Network Interface" block 616, and is coupled to corresponding interface devices in other data processing systems via communication network interface 624. Data processing system 600 could be a terminal or a low-end personal computer or a high-end personal computer, workstation or mainframe.

The user interface input devices typically include a keyboard and may further include a pointing device and a scanner. The pointing device may be an indirect pointing device such as a mouse, trackball, touchpad, or graphics tablet, or a direct pointing device such as a touchscreen incorporated into the display, or a three dimensional pointing device, such as the gyroscopic pointing device described in U.S. Pat. No. 5,440,326, other types of user interface input devices, such as voice recognition systems, can also be used.

User interface output devices typically include a printer and a display subsystem, which includes a display controller and a display device coupled to the controller. The display device may be a cathode ray tube (CRT), a flat-panel device such as a liquid crystal display (LCD), or a projection device. The display subsystem may also provide non-visual displays such as audio output.

Storage subsystem 606 maintains the basic required programming and data constructs. The program modules discussed above are typically stored in storage subsystem 606. Storage subsystem 606 typically comprises memory subsystem 608 and file storage subsystem 614.

Memory subsystem 608 typically includes a number of memories including a main random access memory (RAM) 610 for storage of instructions and data during program execution and a read only memory (ROM) 612 in which fixed instructions are stored. In the case of Macintosh-compatible personal computers, the ROM would include portions of the operating system; in the case of IBM-compatible personal computers, this would include the BIOS (basic input/output system).

File storage subsystem 614 provides persistent (non-volatile) storage for program and data files, and typically includes at least one hard disk drive and at least one floppy disk drive (with associated removable media). There may also be other devices such as a CD-ROM drive and optical drives (all with their associated removable media). Additionally, the system may include drives of the type with removable media cartridges. The removable media cartridges may, for example be hard disk cartridges, such as those marketed by Syquest and others, and flexible disk cartridges, such as those marketed by Iomega. One or more of the drives may be located at a remote location, such as in a server on a local area network or at a site on the Internet's World Wide Web.

In this context, the term "bus subsystem" is used generically so as to include any mechanism for letting the various components and subsystems communicate with each other as intended. With the exception of the input devices and the display, the other components need not be at the same physical location. Thus, for example, portions of the file storage system could be connected via various local-area or wide-area network media, including telephone lines. Similarly, the input devices and display need not be at the same location as the processor, although it is anticipated that personal computers and workstations typically will be used.

Bus subsystem 604 is shown schematically as a single bus, but a typical system has a number of buses such as a local bus and one or more expansion buses (e.g., ADB, SCSI, ISA, EISA, MCA, NuBus, or PCI), as well as serial and parallel ports. Network connections are usually established through a device such as a network adapter on one of these expansion buses or a modem on a serial port. The client computer may be a desktop system or a portable system.

Scanner 620 is responsible for scanning casts of the patient's teeth obtained either from the patient or from an orthodontist and providing the scanned digital data set information to data processing system 600 for further processing. In a distributed environment, scanner 620 may be located at a remote location and communicate scanned digital data set information to data processing system 600 via network interface 624.

Fabrication machine 622 fabricates dental appliances based on intermediate and final data set information received from data processing system 600. In a distributed environment, fabrication machine 622 may be located at a remote location and receive data set information from data processing system 600 via network interface 624.

The system of the present invention is a web-based transaction environment that allows qualified orthodontists and dental practitioners to submit malocclusion cases as candidates for treatment. The system is also used for managing the cases accepted for treatment. The treating professional can accomplish the case submission and case management process entirely within the web-based environment. An orthodontist or treating professional submits cases into a case submission system. The treating professional can also view and manage the case using a case management system. The case management system also interacts with a provider, which operates the system of FIG. 9 in producing aligners for patients based on instructions from the treating professional.

Case submission is the process of creating and submitting a malocclusion case as a candidate for the system's treatment, all within a web-based environment. The orthodontist or treatment professional initiates the case submission process by first logging in to the web application. After a successful login, the treating professional can begin the case creation process. The treating professional enters the patient information, their practice information, the billing and shipping information, and finally the diagnosis and treatment plan. After the case details are finished, the treating professional submits the case information. Subsequently, the treating professional can submit the associated digital images and x-rays. The submitted case is received by the provider. This completes the case submission process.

First, the user clicks on a Start a New Case link to take the user to an On-line Treatment Planning Form where the user can complete the On-line Treatment Planning form and submit the form.

First, the treating professional logs in. The doctor information is updated. Next, patient information is entered. The user can also enter billing information as well as shipping information. Next, the treating professional enters a diagnosis. The treating professional also enters the treatment plan. The case is then submitted. Additionally, digital photographs can be submitted and uploaded to the system of FIG. 10. Also, digital x-ray cells are submitted.

Once the user has submitted the On-line Treatment Planning Form, the user prints copies of the 'Treatment Planning Form Summary', save one copy for the user's records, and place the second copy in the Orthodontics Records box along with the same materials the user typically sends to the system. Next, the user prints a shipping label by clicking on the 'Print UPS Label' button that appears when the user submits a new case on-line. The shipping label is affixed to the outside of an orthodontics records box that contains a Treatment Planning Form Summary, a PVS impression of each arch in a separate foam bag, a bite registration in a separate foam bag, copies of the patient's x-rays, and copies of the patient's photos (intraoral and extraoral), for example.

Case management takes place after the treating professional has submitted the case. The case management process consists of the recursive review and approval process all taking place within the web environment. The case management process ends when the treating professional has finished the closed case.

First, the treating professional submits the case. The system receives the case over the network, and an experienced professional reviewer reviews the case. The completed review is submitted to the server and the treating professional can review and approve the case. Upon receiving the approval, the case manager accepts the case. The case is then forwarded to the system of FIG. 10 to develop a computer model. The computer model is then presented to the case manager, who in turn forwards the model to the treating professional for approval. The treating professional reviews the model and if he or she accepts the treatment plan, sends an approval to the case manager. The system of FIG. 9 then manufactures the aligners. The produced aligners are then shipped to the treating professional. Upon receipt of the fabricated aligners, the treating professional can finish the case. Upon conclusion of treatment, the case is closed and the system of FIG. 10 sends an instruction to the case manager to close the case.

First, a new case is started. This can be done using a treatment planning form. The treatment planning form allows the user to select a case type and to evaluate orthodontic conditions that may be encountered. The process then captures doctor and patient information using a doctor and patient information form. This form verifies address information and shipping information, patient information, and allows the doctor to enter case refinement coverage options, among others. The doctor enters a diagnosis. This can be done through a diagnosis form. The doctor then enters the treatment goals. This can be done using a treatment goals form. The doctor then summarizes the case using a treatment plan summary preview. The case is submitted. This can be done using a treatment plan summary. A shipping label is printed using, for example, a UPS label printing process for cases that are shipped using UPS.

First, a user logs in. In this process, doctor information can be processed. Next, a new case can be started. In this step, case type information can be collected, patient information data can be collected, diagnosis information can be collected, or treatment goals can be collected. The case can be submitted. This can be done over the network. Additional case submission information can also be submitted. X-ray information includes PVS impression, wax bite, x-rays, and digital images, among others. The information from the case submitted and the case submission data is then reviewed. The reviewer can modify, accept, or reject.

FIG. 11 shows an exemplary home page of the web-based interface. The web-based system of FIG. 11 allows users such as doctors to manage the system practices on-line. The user can view all aspects of the patients' cases on-line. The user can also order advertising and marketing materials, chat on-line with other system doctors, review the system's how-to tutorials, and link the user's personal website.

The web-based system helps users such as the treating doctors to ensure that appliances received from the provider will treat the patient the way the user intended. The system does this with a dynamic 3-D animation called a virtual treatment model. The system not only shows the user's patient's teeth going through their projected movement as a result of wearing the system appliances (aligners), but it also gives the user the ability to manipulate the model in time and space to insure the treatment sequence is exactly what the user had in mind. The system gives the user control over the aligners the user will receive: if the animation the user sees does not depict the treatment or outcome the user intended, the system allows the user to send feedback to the provider with instructions on how to re-set the case. After the provider has received the user's explicit approval, the appliances are manufactured and sent to the user's office.

When the user views the case online through the provider's web site (for example at www.invisalign.com), the system contacts the provider's computer systems over the Internet and downloads the treatment model to the user's computer at work or at home. The system then allows the user to play animation showing the treatment progressing over time, starting and stopping at any point during the treatment. It also allows the user to inspect the treatment from any angle, or from as far away or as close as the user likes.

The system allows the user to view the status of all the cases at any point in time. Within the home page, a Patient Chart appears on the right hand side of the page. The chart is divided into two columns—those cases that require action—Action Required—and those that do not—Action Required. Within these lists, a status will appear next to each patient's name. This status identifies the current point of treatment for the patient. For example, if the user has patient John Doe in the Action Required column, and his status reads Awaiting Your Approval, the user will need to view and approve of Mr. Doe's file in order to continue with his treatment.

Status categories that appear under Action Required can include the following:
 Awaiting Approval
 Treatment Form Waiting to be Submitted
 Case Refinement Waiting to be Submitted
 Screening Form Waiting to be Submitted
 Case Screening Result is Ready
 Case on Hold Awaiting New Impressions
 Case Waiting to be Resumed by Doctor
 Midcourse Correction Waiting to be Submitted
 Further Materials Required
 Statuses that can appear under No Action Required include the following:
 Treatment Form Submitted to the provider
 Case Received and Under Review
 Order Accepted by the provider
 Under Development
 Shipments Scheduled
 Aligners Shipped
 Case Refinement Submitted
 Case Currently Being Screened
 Case Hold Requested by Doctor Case Resume Requested by Doctor Cancellation Requested by Doctor Midcourse Correction Submitted Treatment Form Waiting to be Submitted. This means that the user started a standard Online Treatment Planning Form for a patient, but did not submit it to the provider. The case will be stored in VIP under this category until submitting it.

Case Received and Under Review. Case Received and Under Review is a category of patients whose clinical items (Treatment Planning Forms, PVS impressions, Bite Registrations, X-rays, Photos) the provider has received and in the process of confirming that these patients are candidates for the system treatment. If the case is accepted for treatment, the status will change to Order Accepted by the provider. If the case is not accepted for treatment, the status will change to Order Not Accepted by the provider and a representative will call the user's office.

Order Accepted. Order Accepted is a category of patients whose cases have been accepted for treatment by the provider. The next status the user will see for this patient will be Under Development. When this patient's file has been developed, the status will then become Awaiting Approval. At that time, feedback to the system will be required in order to continue processing the case.

Under Development. Under Development is a category of patients whose files are currently being developed by the provider. When the system is ready, the patient's status will change to Awaiting Approval. At that time, feedback to the system will be required in order to continue processing the case.

Awaiting Approval. Awaiting Approval is a category of patients whose files are ready for review and feedback. To review a patient's file, the user can click on their name in the home page. The user will be linked to the patient's Summary Page where the user can view models. If the user accepts a patient's case, the status for the patient will change to The aligner in Production. If the user requests modification of the file, the status will change back to Under Development.

Shipments Scheduled. Shipments Scheduled is a category of patients' whose aligners are currently being produced and are due to ship in the near term. To view a patient's scheduled ship date, the user can click on his or her name. The user will be linked to the patient's Summary Page where the user can view the ship date. Once the patient's aligners are shipped, the status will change to Aligners Shipped.

Aligners Shipped. Aligners Shipped is a category of patients' whose aligners have already shipped. The user can check the date the aligners were shipped by clicking on the patient's name. The user will be linked to the patient's Summary Page where the user can view the ship date. This is the last status for a patient.

Case Refinement Waiting to be Submitted. Case Refinement Waiting to be Submitted is a category of patients whose Case Refinement Form the user started, but did not yet submit to the provider. To submit this form for a patient, the user can click on the patient's name. The user will be linked to the patient's Summary Page. From this page the user can continue filling out the form and submit it to the provider. Once the form is submitted, the status will change to Case Refinement Submitted.

Case Refinement Submitted. Case Refinement Submitted is a category of patients whose Case Refinement Form the user submitted to the provider. Once the provider begins developing a new file for these patients, the patient status will change to Under Development. When the system is ready, the patient's status will change to Awaiting Approval. At that time, feedback to the system will be required in order to continue processing the case.

Screening Form Waiting to be Submitted. Screening Form Waiting to be Submitted is a category of patients' whose Screening Forms the user started, but did not submit to the provider. To submit this form for a patient, a user can click on the patient's name. The user will be linked to the patient's Summary Page. From this page the user can continue filling out the form and submit it to the provider. Once the form is submitted, the status will change to Case Currently Being Screened.

Case Currently Being Screened. Case Currently Being Screened is a category of patients' whose Screening Forms the user submitted to the provider. These cases are currently being reviewed by the provider when the review process is complete, the patient status will change to Case Screening Result is Ready.

Case Screening Result is Ready. Case Screening Result is Ready is a category of patients' whose Screening Forms the user submitted to the provider and whose results are ready for review. These cases are currently being reviewed by the provider—when the review process is complete, the patient status will change to Case Screening Result is Ready. To review the case screening results for a patient, the user can click on the patient's name.

Case on Hold Awaiting New Impressions. Case on Hold Awaiting New Impressions is a category of patients' whose cases have been placed on hold by the provider due to unusable PVS impressions. When the provider places a case on hold, the user's office will be called so that steps can be taken to resume the case as quickly as possible.

Case Waiting to be Resumed by Doctor. Case Waiting to be Resumed by Doctor is a category of patients whose cases the user has placed on hold—these cases will remain on hold until the user resumes them. To resume a case, the user can click on the patient's name in VIP. The user will be linked to the patient's Summary Page. From this page the user can click on the Resume this Case link.

Case Hold Requested by Doctor. Case Hold Requested by Doctor is a category of patients' whose cases the user has requested that The provider hold. Before The provider places the case on hold, the user will be called to confirm that the user wants The provider to stop processing the case. Once The provider has confirmed that the user wants the case placed on hold, the status will change to Case Waiting to be Resumed by Doctor. The user can then resume it by clicking on the patient's name in VIP. The user will be linked to the patient's Summary Page. From this page the user can click on the Resume this Case link.

Case Resume Requested by Doctor. Case Hold Requested by Doctor is a category of patients' whose cases the user has requested that the provider hold. Before the provider places the case on hold, the user's office will be called to confirm that the user wants the provider to stop processing the case. Once the provider has confirmed that the user wants the case placed on hold, the status will change to Case Waiting to be Resumed by Doctor. The user can then resume it by clicking on the patient's name. The user will be linked to the patient's Summary Page. From this page the user can click on the Resume this Case link.

Cancellation Requested by Doctor. Cancellation Requested by Doctor is a category of patients' whose cases the user has requested that the provider cancel. Before the provider cancels a case, the user's office will be called to confirm that the user wants the provider to stop processing the case. Once the provider has confirmed that the user wants the case placed on hold, the case will be removed from the database.

Midcourse Correction Waiting to be Submitted. Midcourse Correction Form Waiting to be Submitted is a category of patients whose Midcourse Correction Forms the user started, but did not submit to the provider. To submit this form for a patient, the user can click on the patient's name. The user will be linked to the patient's Summary Page. From this page the user can continue filling out the form and submit it to the provider. Once the form is submitted, the status will change to Midcourse Correction Submitted. Once the provider has had a chance to review the user's request, the patient status will change to Under Development.

Midcourse Correction Submitted. Midcourse Correction Submitted is a category of patients' whose Midcourse Correction Forms the user recently submitted to the provider. Once the provider has had a chance to review the request, the patient status will change to Under Development.

Further Materials Required. Further Materials Required is a category of patients' whose files are incomplete and cannot be processed further until additional materials are sent to the provider. In most cases, this means that the Submission Box sent to the provider did not include all necessary patient materials. When a case enters this status, the provider will call the user's office to let the user know that further materials are required.

To view only certain cases, the user must click on the status category in the Case Summary box that the user is interested in viewing. For example, if the user would like to view only cases that are in the Awaiting Approval phase, the user clicks on that link. The patient chart on the right side of the page will now only display cases in the Awaiting Approval phase.

To return to a view of all the cases, the user clicks on Total to take the user back to the original patient chart. The user can also sort cases within any patient list by clicking on one of the column headings. For example, to sort cases by patient name, the user must click on the Patient Name heading. The cases will now be sorted in alphabetical order by patient name. The user can always identify how the patient list is sorted by noting which column heading is italicized.

Each of the patients in treatment has their own Patient Summary Page. The Patient Summary Page allows the user to view all aspects of a patient's case, from their file to their treatment history. To access a Patient's Summary Page, the user clicks on the name of the patient whose file the user would like to view. The user can find a list of all the patients on the Home Page. From the Patient Summary Page, the user can do each of the following:

View a Patient's Model
View Static Images
View Treatment History
View On-line Forms—Attachment and Reproximation
Create an Aligner Schedule
Place a Case on Hold
Cancel a Case One function supported by the system is to enable the user to complete an On-line Treatment Planning Form as quickly and as efficiently as possible.

On the Treatment Forms page the user can access the following:
On-line Treatment Planning Form
Paper Treatment Planning Form
Case Refinement Form
Mid-course Correction Form A template called Treatment Preferences shown in FIG. 12 is used and allows the user to enter treatment information one time—this information is then incorporated into each form the user fills out, eliminating the need to enter redundant information each time the user submits a new case. The Treatment Preferences form will automatically appear in a separate window when the user clicks on the Start a New Case link for the first time. For each On-line Treatment Planning Form the user fills out, at the beginning of the form the user will be given the option of activating the Treatment Preferences for that form. The user can change the Treatment Preferences at any time by clicking on the Treatment Preferences link that appears after the user has clicked on the Start a New Case link.

In this system, the form does not allow the user to advance to subsequent pages until the current page is completely filled out. In addition, the form has built-in logic; it does not permit the user to send in a form that has contradicting inputs, nor can the user submit a case that does not meet predetermined case selection criteria. These features greatly increase the likelihood that each submitted case would be accepted for treatment. If the user needs help filling out the form, the user clicks on the question mark symbol within the form to view the comprehensive Help section.

Yet another feature is a Case Selection Expansion option. Case Selection Expansion allows experienced system doctors to submit cases beyond the limits of what is normally accepted through the On-line Treatment Planning Form. If the user is an experienced user who has submitted a large number of cases, the user is eligible for Case Selection Expansion. Once classified as an experienced user, the user will see a screen asking whether the user would like to use the standard On-line Treatment Planning Form or the Case Selection Expansion Form, which allows more flexibility. If the user selects the Case Selection Expansion Form, the user is prompted to sign a waiver. Besides relaxed case selection criteria for the Case Selection Expansion Form, the user will find the two submission forms are identical.

Yet another feature in this embodiment is case screening. If the user is not sure whether a case is appropriate for system treatment and would like feedback from the system, the user can use the Case Screening feature. The user must be able to submit digital photos on-line to use this feature. In one embodiment, to screen a new case, the user clicks on a Case Screening link, enters the office information and the patient's information, enters the treatment plan and goals for the patient, and uploads digital photos of the case—either individual photos or a composite photo. After submission, a professional reviewer at the provider reviews and provides comments and/or suggestions for treatment. If a patient's screening result is ready, that patient's status is listed as Case Screening Result is Ready. The user can then click on the patient's name to view the screening result and to submit the case for treatment.

The system can also handle case refinement situations. Case refinement occurs when additional aligners beyond the last stage are needed to move a patient's teeth closer to the desired final outcome approved by the user in the system. If the user has a case that qualifies for Case Refinement, the user's next step is to submit a Case Refinement Form for that case. Once the user has submitted a Case Refinement Form, the user can track the status of the form through the VIP Home Page. When the form is submitted, the patient's status will change to Case Refinement Submitted. When a new file begins production, the status will change to Under Development. Once the file is ready for review, the status will change again to Awaiting Approval.

In instances when clinical results deviate from the original treatment plan such that the aligner(s) no longer fit, a Mid-Course Correction is necessary. This may be due to any of the following:

Patient underwent dental work during the course of treatment

Poor patient compliance

Treatment goal has changed

Case has deviated from the approved course of treatment

If the user has a case that qualifies for Mid-Course Correction, the next step is to submit a Mid-Course Correction Form for that case. Once the user has submitted a Mid-Course Correction Form, the user can track the status of the form through the Home Page.

When the form is submitted, the patient's status will change to Mid-Course Correction Form Submitted. When a new file begins production, the status will change to Under Development. Unlike Case Refinement Cases, Mid-Course Correction files do not require feedback. Once the file is ready, the status will change again to Aligner Shipments Scheduled.

Figure 13A:
FIGS. 13A and 13B are exemplary drawings of a patient's teeth depicting initial and final high resolution images.
Figure 13B:
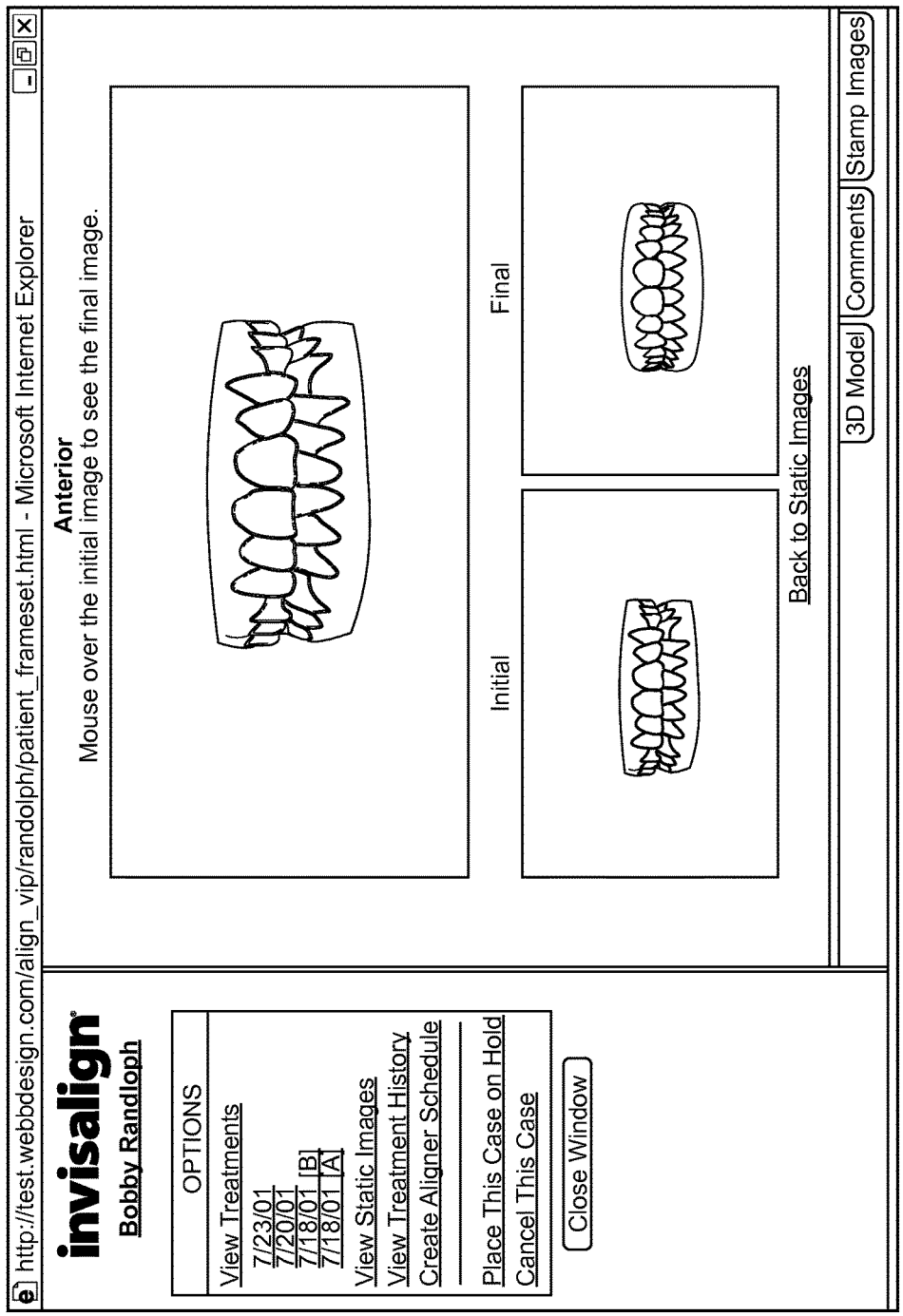

FIGS. 13A and 13B show exemplary views of Static Images of a patient's teeth. The benefit of the Static Images is that they provide the user with initial and final images of the depicted treatment at a high resolution. To view a patient's Static Images, the user can click on the View Static Images link within the Options left menu bar on the left side of a Patient's Summary Page. Alternatively, the user can access Static Images by clicking on the Static Images link at the bottom a Patient's Summary Page. Once viewing the images, the user can enlarge them for a better view by clicking on them.

FIG. 13B shows a Scroll Over Model—the user can scroll the mouse over the image to view the initial and final views of the patient's depicted treatment. The bottom images provide a side-by-side comparison of the initial and final views.

The system can also allow the user to view a patient's dental model. To view a patient's file, the user must click on the name of the patient whose file the user would like to view. The user can use the system to see many different views of a treatment model. The user can zoom in and out, hide the upper and lower arches, and rotate the model to see it from different angles. The user can choose to see the model from fourteen different pre-set angles. The user can rotate a model to any angle, making it seem to spin in the window. The user can position the mouse inside the model window and click and hold the left mouse button while dragging the mouse in the direction that the user wants to move the model. The model rotates as the user moves the mouse. As an example, the user can start with the right buccal view of the model. The user must click and hold the left mouse button and drag the mouse from right to left. As the user does so, the model rotates so the user can see all of the teeth as the model moves.

If the user would like to take a closer look at a model, the user can zoom in. Conversely, if the user would like to see a view of the model from further away, the user can zoom out. To zoom, the user must press and hold the Control (Ctrl) key. Positioning the mouse inside the model window, the user must click and hold the left mouse button and drag the mouse up to zoom out and down to zoom in. The further the user drags, the further the user will zoom. Alternatively, if the mouse has a mouse wheel, the user can turn the mouse wheel to zoom in and out. The user can also slide the model up and down, and left and right. To slide the model, the user must press and hold the Shift key, then click and drag the mouse. The model moves in the direction of the mouse motion. This motion can be useful when the user has a zoomed in view of the model, and the user would like to see another part of the model. The user can hide the upper or lower arch to see an unobstructed view of the other arch. This is useful, for example, when looking at the occlusal surface of either arch. To hide the upper arch, the user must click the checked box next to Show Upper Jaw in the left menu bar. The check mark is removed and the upper arch disappears from view. To hide the lower arch, the user must click the checked box next to Show Lower Jaw in the Dialog box. The check mark is removed and the lower arch disappears from view. When the user hides either arch, the user can still rotate the model so the user can see it from any angle. Once the user has hidden an arch, the user can show it again. To show an arch once the user has hidden it, the user must re-select the Show Upper Jaw or Show Lower Jaw command from the left bar menu. When the boxes show check marks, the arches are shown. The user can also select the level of detail of the model. On the left menu bar, the options Show Low Resolution and Show High Resolution appear. By default, Show Low Resolution is selected. Alternatively, the user can select Show High Resolution to show a more detailed version of the model.

To print a model in its current view, the user must click the Print icon or right-click the mouse over the window and select Print from the Right Mouse Button menu.

The animation allows the user to see how a patient is projected to progress using the system. Using the animation controls located in the lower right corner of the model window, the user can play, stop, rewind and fast-forward the animation. The user can also step forward or backward through the animation stage by stage (a stage corresponds to one set of aligners). To play an animation, the user must click the Play button. The Play button then becomes the Stop button. To stop an animation, the user must click the Stop button. To resume playing the animation, the Play button is clicked. When the user rewinds an animation, the model returns to its beginning position. To rewind an animation, the user can click the Rewind (<<) button. To rewind the model stage-by-stage, the user can click the Back (<) button and the model will rewind one stage. When the user fast-forwards an animation, the model advances to its final position. To fast-forward an animation, the user can click the Fast Forward (>>) button. To view the model stage-by-stage, the user can click the Forward (>) button and the model will advance one stage.

Other features supported by the web-based system of the present invention includes Viewing Current/Archived News; Viewing the Case Gallery where the user can view before and after pictures of past system patients by visiting the system Case Gallery; Downloading All Files at Once, where the user can view the patients' cases without being connected to the Internet; Printing a List of All Patients; and a Message Board, where the users talk with other system doctors to share experiences with the product so the user can learn from and offer suggestions to other doctors who are using the provider.

The invention has been described in terms of particular embodiments. Other embodiments are within the scope of the following claims. For example, the three-dimensional scanning techniques described above may be used to analyze material characteristics, such as shrinkage and expansion, of the materials that form the tooth castings and the aligners. Also, the 3D tooth models and the graphical interface described above may be used to assist clinicians that treat patients with conventional braces or other conventional orthodontic appliances, in which case the constraints applied to tooth movement would be modified accordingly.

What is claimed is:

1. A system for manufacturing orthodontic appliances, the system comprising:
   a server comprising storage media having one or more instructions that when executed cause the server to:
   receive digitized data representing the patient's teeth and case type data for the patient;
   process the digitized data and the case type data so as to generate one or more manipulable three-dimensional computer models of the patient's teeth, the one or more manipulable three-dimensional computer models representing a sequential treatment plan for the patient's teeth;
   transmit the one or more manipulable three-dimensional computer models representing the sequential treatment plan to a computer associated with one or more treating professionals;
   receive, from the computer associated with the one or more treating professionals, feedback data including either one of: (a) an adjustment to a tooth position in at least one of the one or more manipulable three-dimensional computer models of the patient's teeth, or (b) an approval of the sequential treatment plan; and
   process the feedback data so as to generate a plurality of digital data sets for manufacturing a plurality of sequential orthodontic appliances; and
   a fabrication machine configured to:
   receive at least one of the plurality of digital data sets; and
   manufacture at least one of the plurality of sequential orthodontic appliances based on the digital data sets.

2. The system of claim 1, wherein the case type data comprises information on the patient's malocclusion.

3. The system of claim 1, wherein the feedback data includes the adjustment to the tooth position in the at least one of the one or more manipulable three-dimensional computer models.

4. The system of claim 3, wherein the adjustment of the tooth position in the at least one of the one or more manipulable three-dimensional computer models comprises automated teeth collision detection.

5. The system of claim 1, wherein the one or more manipulable three-dimensional computer models of the patient's teeth correspond to an initial arrangement, one or more intermediate arrangements, and a desired final arrangement of the patient's teeth in the sequential treatment plan.

6. The system of claim 5, wherein the one or more manipulable three-dimensional computer models of the patient's teeth are configured to be displayed as one or more animations of the patient's teeth from the initial arrangement to one or more intermediate arrangements or the desired final arrangement.

7. The system of claim 1, wherein the one or more manipulable three-dimensional computer models of the patient's teeth are configured to visually display an expected outcome of the sequential treatment plan.

8. The system of claim 1, wherein at least one of the one or more treating professionals is a dentist or an orthodontist.

9. The system of claim 1, wherein the server is coupled to the computer associated with the one or more treating professionals over a network.

10. The system of claim 9, wherein the network is accessible by the computer associated with the one or more treating professionals using a browser.

11. A method for manufacturing orthodontic appliances, the method comprising:
    receiving, by a computer system that includes one or more processors, digitized data representing the patient's teeth and case type data for the patient;
    processing, by the computer system, the digitized data and the case type data so as to generate one or more manipulable three-dimensional computer models of the patient's teeth, the one or more manipulable three-dimensional computer models representing a sequential treatment plan for the patient's teeth;
    transmitting the one or more manipulable three-dimensional computer models representing the sequential treatment plan to a computer associated with one or more treating professionals;
    receiving, from the computer associated with the one or more treating professionals, feedback data including at least one of: (a) an approval of the sequential treatment plan, or (b) an adjustment to a tooth position in at least one of the one or more manipulable three-dimensional computer models;
    processing, by the computer system, the feedback data so as to generate a plurality of digital data sets for manufacturing a plurality of sequential orthodontic appliances;
    transmitting, to a fabrication machine, the plurality of digital data sets for manufacturing a plurality of sequential orthodontic appliances; and
    manufacturing, by the fabrication machine, at least one of the plurality of sequential orthodontic appliances based on at least one of the plurality of digital data sets.

12. The method of claim 11, wherein the case type data comprises information on the patient's malocclusion.

13. The method of claim 11, wherein the feedback data includes the adjustment to the tooth position in the at least one of the one or more manipulable three-dimensional computer models.

14. The method of claim 13, wherein the adjustment of the tooth position in the at least one of the one or more manipulable three-dimensional computer models comprises using automated teeth collision detection.

15. The method of claim 11, wherein the one or more manipulable three-dimensional computer models of the patient's teeth correspond to an initial arrangement, one or more intermediate arrangements, and a desired final arrangement of the patient's teeth in the sequential treatment plan.

16. The method of claim 15, further comprising generating one or more animations of the patient's teeth from the initial arrangement to one or more intermediate arrangements or the desired final arrangement.

17. The method of claim 11, further comprising visually displaying an expected outcome of the sequential treatment plan.

18. The method of claim 11, wherein the one or more treating professionals comprise at least one of a dentist or an orthodontist.

19. The method of claim 11, wherein the computer system is coupled to the computer associated with the one or more treating professionals over a network.

20. The method of claim 19, wherein the network is accessible by the computer associated with the one or more treating professionals using a browser.

* * * * *